US012385082B2

(12) United States Patent
Gilly et al.

(10) Patent No.: US 12,385,082 B2
(45) Date of Patent: Aug. 12, 2025

(54) TEMPERATURE-SELECTABLE FRET CASSETTE SIGNALING

(71) Applicant: GEN-PROBE INCORPORATED, San Diego, CA (US)

(72) Inventors: Michael J. Gilly, San Diego, CA (US); Ankur H. Shah, San Diego, CA (US); Andrew S. Gilder, San Diego, CA (US)

(*) Notice: Subject to any disclaimer, the term of this patent is extended or adjusted under 35 U.S.C. 154(b) by 0 days.

(21) Appl. No.: 18/939,315

(22) Filed: Nov. 6, 2024

(65) Prior Publication Data

US 2025/0075254 A1 Mar. 6, 2025

Related U.S. Application Data

(62) Division of application No. 18/694,253, filed as application No. PCT/US2022/077243 on Sep. 29, 2022.

(60) Provisional application No. 63/250,894, filed on Sep. 30, 2021.

(51) Int. Cl.
 *C12Q 1/6823* (2018.01)
 *C12Q 1/6844* (2018.01)

(52) U.S. Cl.
 CPC ......... *C12Q 1/6823* (2013.01); *C12Q 1/6844* (2013.01)

(58) Field of Classification Search
 None
 See application file for complete search history.

(56) References Cited

U.S. PATENT DOCUMENTS

| | | | |
|---|---|---|---|
| 10,590,469 | B2 | 3/2020 | Gupta et al. |
| 11,034,997 | B2 | 6/2021 | Kozlov et al. |
| 11,198,903 | B2 | 12/2021 | Kozlov et al. |
| 2013/0231256 | A1 | 9/2013 | Oldham-Haltom et al. |
| 2014/0272955 | A1 | 9/2014 | Gupta |
| 2015/0072887 | A1 | 3/2015 | Chun et al. |
| 2018/0073064 | A1 | 3/2018 | Kozlov et al. |
| 2018/0163259 | A1 | 6/2018 | Peterson et al. |

FOREIGN PATENT DOCUMENTS

| | | |
|---|---|---|
| EP | 3237636 | 10/2020 |
| EP | 3512960 | 10/2022 |
| WO | WO 2010/013017 | 2/2010 |
| WO | WO-2014158628 A1 | 10/2014 |
| WO | WO 2014/205083 | 12/2014 |
| WO | WO 2015/147370 | 10/2015 |
| WO | WO 2016/101959 | 6/2016 |
| WO | WO-2016179093 A1 | 11/2016 |
| WO | WO 2018/050828 | 3/2018 |
| WO | WO 2021/055508 | 3/2021 |

OTHER PUBLICATIONS

Howell, iFRET: An Improved Fluorescence System for DNA-Melting Analysis, Genome Research, 12(9): 1401-1407, 2002. (Year: 2002).*
Ahrberg et al., Doubling Throughput of a Real-Time PCR. Sci Rep. Jul. 27, 2015:5:12595.
Examination Report for AU2022357542, mailed Mar. 6, 2024, 3 pages.
Examination Report for EP 17768768.8, mailed Jun. 12, 2020, 7 pages.
Lee et al., Single-channel multiplexing without melting curve analysis in real-time PCR. Sci Rep. Dec. 11, 2014:4:7439.
Lee et al., Single-channel multiplexing without melting curve analysis in real-time PCR. Sci Rep. Dec. 11, 2014:4:7439, Supplementary Information.
Office Action for CA 3232383, mailed Apr. 19, 2024, 6 pages.
Oliver, The Invader® assay for SNP genotyping. Mutat Res. Jun. 3, 2005;573(1-2):103-110.
Ririe et al., Product differentiation by analysis of DNA melting curves during the polymerase chain reaction. Anal Biochem. Feb. 15, 1997;245(2):154-60.
Roche Applied Science, LightCycler® 480 Instrument Operator's Manual, Software Version 1.5, 2008, 395 pages.
Ross et al., Temperature measurement in microfluidic systems using a temperature-dependent fluorescent dye. Anal Chem. Sep. 1, 2001;73(17):4117-23.
Sanford et al., Monitoring temperature with fluorescence during real-time PCR and melting analysis. Anal Biochem. Mar. 1, 2013;434(1):26-33.
Seegene, MuDT™ Technology video. Retrievable at www.seegene.com/video_library/2015_mudt_technology_full, 2015.
International Search Report mailed Jan. 30, 2023, issued in corresponding Application No. PCT/US2022/077243, filed Sep. 29, 2022, 4 pages.
Final Office Action for U.S. Appl. No. 18/694,253, mailed Feb. 24, 2025, 11 Pages.
Lou et al., "Fluorescence-Based Thermometry: Principles and Applications," Reviews in Analytical Chemistry, 1999, vol. 18, No. 4, pp. 235-284.
Non-Final Office Action for U.S. Appl. No. 18/939,319, mailed Jan. 13, 2025, 10 Pages.
Non-Final Office Action for U.S. Appl. No. 18/939,321, mailed Jan. 30, 2025, 10 Pages.

* cited by examiner

*Primary Examiner* — Samuel C Woolwine
*Assistant Examiner* — Carolyn L Greene
(74) *Attorney, Agent, or Firm* — Casimir Jones, S.C.; Mary Ann D. Brow

(57) ABSTRACT

A multiplexed nucleic acid amplification and detection system useful for detecting the presence of multiple specific nucleic acid sequences or single nucleotide polymorphisms (i.e., "SNPs") in a temperature-dependent fashion using only a single fluorescence detection channel of a nucleic acid analyzer. The technique can be carried out using standard PCR instrumentation equipped for fluorescence detection or monitoring.

18 Claims, 10 Drawing Sheets

Specification includes a Sequence Listing.

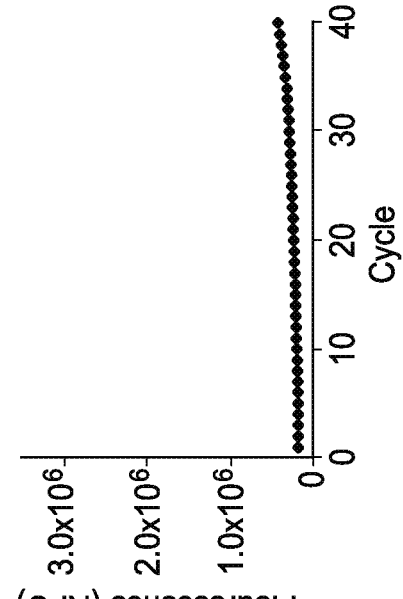
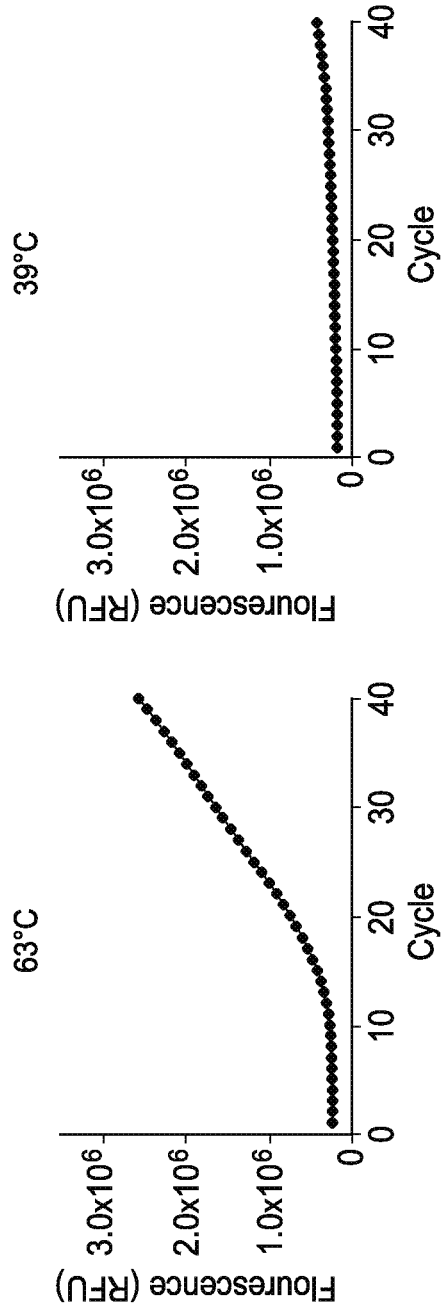
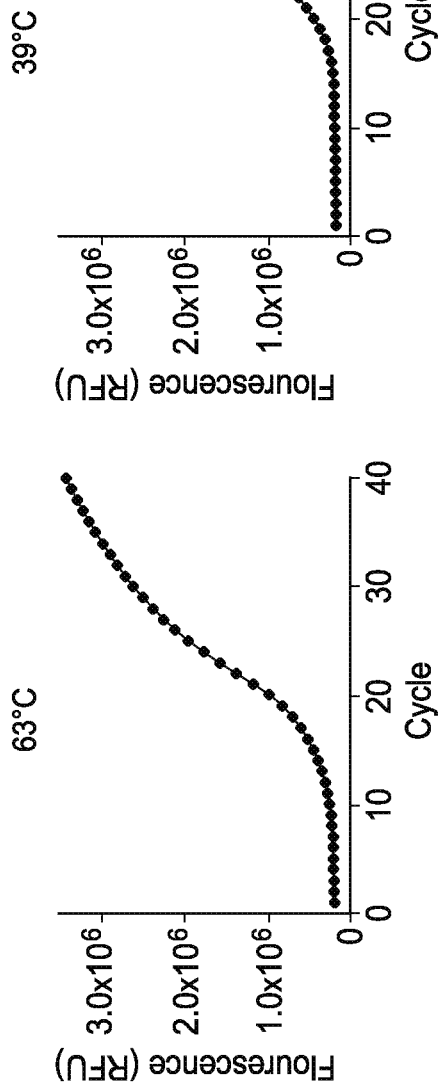
FIG. 7A  FIG. 7B  FIG. 7C  FIG. 7D

SEQUENCE LISTING

```
Sequence total quantity: 16
SEQ ID NO: 1              moltype =    length =
SEQUENCE: 1
000

SEQ ID NO: 2              moltype = DNA  length = 31
FEATURE                   Location/Qualifiers
source                    1..31
                          mol_type = other DNA
                          organism = synthetic construct
misc_feature              14..31
                          function = Complementary to positions 22-39 of SEQ ID NO:3
                           (Target strand nucleic acid)
misc_feature              31
                          function = 3'-hexanediol
SEQUENCE: 2
acgggacgcg gagnnnnnnn nnnnnnnnnn n                                              31

SEQ ID NO: 3              moltype =    length =
SEQUENCE: 3
000

SEQ ID NO: 4              moltype = DNA  length = 14
FEATURE                   Location/Qualifiers
source                    1..14
                          mol_type = other DNA
                          organism = synthetic construct
misc_feature              1..13
                          function = Complementary to positions 27-39 of SEQ ID NO:5
                           (FRET cassette)
SEQUENCE: 4
acgggacgcg gagn                                                                 14

SEQ ID NO: 5              moltype = DNA  length = 39
FEATURE                   Location/Qualifiers
source                    1..39
                          mol_type = other DNA
                          organism = synthetic construct
misc_feature              1
                          function = 5' HEX fluorophore
misc_feature              3..4
                          function = Quencher moiety joined to oligo between base
                           positions 3 and 4
misc_feature              4..11
                          function = Complementary to positions 16-23 in a hairpin
                           configuration
misc_feature              39
                          function = 3'-hexanediol
SEQUENCE: 5
tctnnnnnnn ntttnnnnn nnnagactcc gcgtcccgt                                       39

SEQ ID NO: 6              moltype = DNA  length = 38
FEATURE                   Location/Qualifiers
source                    1..38
                          mol_type = other DNA
                          organism = synthetic construct
misc_feature              2..3
                          function = Quencher moiety joined to oligo between base
                           positions 2 and 3
misc_feature              3..10
                          function = Complementary to positions 15-22 in a hairpin
                           configuration
misc_feature              38
                          function = 3'-hexanediol
SEQUENCE: 6
ctnnnnnnnn ttttnnnnnn nnagactccg cgtcccgt                                       38

SEQ ID NO: 7              moltype = DNA  length = 46
FEATURE                   Location/Qualifiers
source                    1..46
                          mol_type = other DNA
                          organism = synthetic construct
misc_feature              10
                          function = HEX fluorophore joined to oligonucleotide at
                           position 10
misc_feature              13..14
                          function = Quencher moiety joined to oligo between base
                           positions 13 and 14
```

```
misc_feature              14..21
                          function = Complementary to positions 26-33 in a hairpin
                           configuration
misc_feature              37..46
                          function = Complementary to positions 1-10 of SEQ ID NO:8
                           (cleaved flap from primary probe)
misc_feature              46
                          function = 3'-hexanediol
SEQUENCE: 7
caactgtatg tctnnnnnnn nttttnnnnn nnnagacctc ggcgcg                              46

SEQ ID NO: 8              moltype = DNA   length = 11
FEATURE                   Location/Qualifiers
source                    1..11
                          mol_type = other DNA
                          organism = synthetic construct
misc_feature              1..10
                          function = Complementary to positions 37-46 of SEQ ID NO:7
                           (5' flap FRET cassette)
SEQUENCE: 8
cgcgccgagg n                                                                   11

SEQ ID NO: 9              moltype = DNA   length = 11
FEATURE                   Location/Qualifiers
source                    1..11
                          mol_type = other DNA
                          organism = synthetic construct
misc_feature              10
                          function = Position 10 modified with HEX fluorophore
SEQUENCE: 9
caactgtatg t                                                                   11

SEQ ID NO: 10             moltype = DNA   length = 10
FEATURE                   Location/Qualifiers
source                    1..10
                          mol_type = other DNA
                          organism = synthetic construct
misc_feature              1
                          function = 5' quencher moiety
SEQUENCE: 10
catacagttg                                                                     10

SEQ ID NO: 11             moltype = DNA   length = 34
FEATURE                   Location/Qualifiers
source                    1..34
                          mol_type = other DNA
                          organism = synthetic construct
misc_feature              1
                          function = 5' HEX fluorophore
misc_feature              3..4
                          function = Quencher moiety joined to oligo between base
                           positions 3 and 4
misc_feature              4..9
                          function = complementary to positions 14-19 in a hairpin
                           configuration
misc_feature              23..34
                          function = Complementary to positions 1-12 of SEQ ID NO:12
                           (cleaved flap from Target 1)
misc_feature              34
                          function = 3'-hexanediol
SEQUENCE: 11
tctnnnnnnt tttnnnnnna gacgtccgtg gcct                                          34

SEQ ID NO: 12             moltype = DNA   length = 13
FEATURE                   Location/Qualifiers
source                    1..13
                          mol_type = other DNA
                          organism = synthetic construct
misc_feature              1..12
                          function = Complementary to positions 23-34 of SEQ ID NO:11
                           (flapless FRET cassette)
SEQUENCE: 12
aggccacgga cgn                                                                 13

SEQ ID NO: 13             moltype = DNA   length = 48
FEATURE                   Location/Qualifiers
source                    1..48
                          mol_type = other DNA
                          organism = synthetic construct
```

```
misc_feature           10
                       function = Position 10 modified with HEX fluorophore
misc_feature           13..14
                       function = Quencher moiety joined to oligo beetween base
                         positions 13-14
misc_feature           14..21
                       function = Complementary to positions 26-33 in a hairpin
                         configuration
misc_feature           37..48
                       function = Complementary to positions 1-12 of SEQ ID NO:14
                         (cleaved flap from Target 3 primary probe)
misc_feature           48
                       function = 3'-hexanediol
SEQUENCE: 13
cagctgcatg tctnnnnnnn nttttnnnnn nnnagactcc gcgtccgt                  48

SEQ ID NO: 14          moltype = DNA  length = 13
FEATURE                Location/Qualifiers
source                 1..13
                       mol_type = other DNA
                       organism = synthetic construct
misc_feature           1..12
                       function = Complementary to positions 37-48 of SEQ ID NO:13
                         (5' flap FRET cassette 2)
SEQUENCE: 14
acggacgcgg agn                                                       13

SEQ ID NO: 15          moltype = DNA  length = 11
FEATURE                Location/Qualifiers
source                 1..11
                       mol_type = other DNA
                       organism = synthetic construct
misc_feature           1..10
                       function = Complementary to positions 1-10 of SEQ ID NO:16
                         (masking oligo 2)
misc_feature           10
                       function = Position 10 modified with HEX fluorophore
SEQUENCE: 15
cagctgcatg t                                                         11

SEQ ID NO: 16          moltype = DNA  length = 10
FEATURE                Location/Qualifiers
source                 1..10
                       mol_type = other DNA
                       organism = synthetic construct
misc_feature           1..10
                       function = Complementary to positions 1-10 of SEQ ID NO:15
                         (cassette cleaved flap 2)
misc_feature           1
                       function = 5' quencher moiety
SEQUENCE: 16
catgcagctg                                                           10
```

TEMPERATURE-SELECTABLE FRET CASSETTE SIGNALING

CROSS-REFERENCE TO RELATED APPLICATIONS

This application is a divisional of U.S. application Ser. No. 18/694,253, filed Mar. 21, 2024, which is a national stage of International Application No. PCT/US2022/077243, filed Sep. 29, 2022, which claims the benefit under 35 U.S.C. § 119(e) of U.S. Provisional Application No. 63/250,894, filed Sep. 30, 2021. The entire disclosure of each earlier application is incorporated herein by reference.

SEQUENCE LISTING

The text of the computer readable sequence listing filed herewith, titled "39302-403_SEQUENCE_LISTING", created Apr. 16, 2022, having a file size of 27,886 bytes, is hereby incorporated by reference in its entirety.

TECHNICAL FIELD

The disclosure relates generally to the field of biotechnology. More specifically, the disclosure relates to compositions, methods, kits, and systems for detecting and distinguishing different analyte nucleic acids using invasive cleavage reactions and a single fluorescent detection channel.

BACKGROUND

The quantification of nucleic acids plays an important role in the fields of biology and medicine. For example, quantification of nucleic acid is used in cancer diagnosis and prognosis, and in the diagnosis and monitoring of infectious diseases caused by bacterial, fungal, and viral pathogens.

There is great value in detecting multiple nucleic acid analytes in a single reaction mixture. Indeed, so-called "multiplex" detection greatly enhances the value of a nucleic acid assay while reducing associated reagent costs. However, different assay formats accommodate multiplexing capabilities to different extents, meaning that there are practical trade-offs. For example, next generation sequencing technology permits acquisition of vast amounts of information, but that technique is technically very challenging and generally requires highly specialized equipment. Another technique, referred to as the "invasive cleavage assay," permits nucleic acid sequence detection down to the level of single nucleotide differences ("SNPs"), and has already been used in connection with some multiplex assay formats.

For example, Hall et al., in U.S. Pat. No. 5,994,069 described two multiplexing approaches useful in connection with invasive cleavage detection methods. First, the presence of a particular target sequence (or internal control) can be designed to trigger a different cascade coupled to different detectable moieties, such as different dyes in a fluorescence energy transfer format. The contribution of each specific target sequence to a final product can be tallied, allowing quantitative detection of different nucleic acid sequences contained in a mixture of nucleic acid sequences. In a second configuration, it is desirable to determine if any of several analytes are present in a sample but the exact identity of each does not need to be known. For example, in blood banking it is desirable to know if any one of a host of infectious agents is present in a sample of blood. Because the blood is discarded regardless of which agent is present, different signals being produced by the different probes would not be required in such an application, and may actually be undesirable for reasons of confidentiality. Thus, a single detectable label can be used when it is unnecessary or undesirable to distinguish between analytes.

Elsewhere, Peterson et al., in published U.S. patent application 2018/0163259 A1, describe detection of different nucleic acid analytes by conducting secondary invasive cleavage reactions at different temperatures and at different times. Here the first secondary invasive cleavage reaction is complete by the time the second secondary invasive cleavage reaction begins. By conducting the reactions at different times under different temperatures, it is possible to distinguish nucleic acid analytes in a single multiplex reaction.

Using a different assay format, Kozlov et al., in U.S. Pat. No. 11,034,997 instruct methods for performing multiplexed real-time PCR for detection and quantitation of target nucleic acids using tagged hydrolysis probes. A single probe cleavage event occurs with each cycle of the PCR reaction as the polymerase having 5'-to-3' exonuclease activity cleaves the tag portion and hydrolyzes the remaining portion of the probe. When the tag harbors a fluorophore that becomes separated from a quencher on the annealing portion of the probe, a fluorescent signal can be generated. Fluorescent label associated with an oligonucleotide probe that hybridized to the target nucleic acid can be cleaved from the target-complementary portion of the probe, which subsequently is degraded, during one cycle of the primer extension (i.e., polymerization) reaction. Consequently, increasing signal strength depends on performing additional cycles of the PCR reaction. As well, Kozlov et al., teach that a "quenching molecule" (e.g., an oligo) hybridizes to the tag portion of uncleaved hydrolysis probes at the temperature used for extending primers in the primer extension reaction of the PCR. Prior to the primer extension cycle in the PCR reaction, fluorescence is quenched by the quencher moiety joined to the annealing portion of the probe and to the quenching molecule.

Despite availability of existing nucleic acid multiplex detection platforms, there remains a need for additional approaches that easily can be adapted to automated testing platforms. More particularly, there is a need to maximize the detection capacity of deployed testing instruments without requiring hardware changes.

SUMMARY

Provided herein are the following numbered embodiments.

Embodiment 1 is a composition comprising a FRET cassette reporter system, the composition comprising: (i) a 5' flap FRET cassette oligonucleotide comprising: a 5' flap portion comprising a first fluorophore moiety, a stem-loop portion comprising a first quencher moiety, and a 3' portion comprising a cleaved flap-hybridizing sequence, wherein hybridization of a cassette-specific invasive oligonucleotide complementary to the cleaved flap-hybridizing sequence of the 5' flap FRET cassette oligonucleotide forms an invasive cleavage structure cleavable by a FEN-1 endonuclease at a cleavage site between the first fluorophore moiety and the first quencher moiety, wherein cleavage of the 5' flap FRET cassette oligonucleotide at the cleavage site produces a cassette cleaved flap comprising the 5' flap portion and the first fluorophore moiety; and (ii) a masking oligonucleotide comprising a second quencher moiety, wherein at least a portion of the masking oligonucleotide is specifically hybridizable to the 5' flap portion of the FRET cassette oligonucleotide, wherein hybridization of the masking oligonucleotide to the cassette cleaved flap forms a duplex having a first melting temperature exhibiting a first melting peak, and wherein fluorescence emission from the first fluorophore moiety in the duplex is quenched by the second quencher moiety.

Embodiment 2 is the composition of embodiment 1, wherein the first quencher moiety and the second quencher moiety are the same as each other.

Embodiment 3 is the composition of either embodiment 1 or embodiment 2, further comprising a FEN-1 endonuclease.

Embodiment 4 is the composition of embodiment 3, wherein the FEN-1 endonuclease is a thermostable FEN-1 endonuclease.

Embodiment 5 is the composition of embodiment 4, wherein the thermostable FEN-1 endonuclease is from an archaeal organism.

Embodiment 6 is the composition of any one of embodiments 1 to 5, further comprising a first target-specific invasive oligonucleotide and a first target-specific primary probe oligonucleotide, wherein each of the first target-specific invasive oligonucleotide and the first target-specific primary probe oligonucleotide comprise sequences configured to hybridize to a target nucleic acid to form an invasive cleavage structure cleavable by a FEN-1 endonuclease to produce a primary cleaved flap, and wherein the primary cleaved flap is a cassette-specific invasive oligonucleotide configured to hybridize to the cleaved flap-hybridizing sequence of the 5' flap FRET cassette oligonucleotide to form an invasive cleavage structure cleavable by the FEN-1 endonuclease.

Embodiment 7 is the composition of embodiment 6, further comprising the target nucleic acid.

Embodiment 8 is the composition of embodiment 7, further comprising deoxynucleoside triphosphates (dNTPs), a thermostable DNA polymerase, and primers having 3' ends extendable by the thermostable DNA polymerase using the target nucleic acid as template in a template-dependent nucleic acid amplification reaction.

Embodiment 9 is the composition of any one of embodiments 1 to 8, further comprising: (iii) a second FRET cassette oligonucleotide comprising a 5' portion comprising a second fluorophore moiety, a stem-loop portion comprising a third quencher moiety, and a 3' portion comprising a second cleaved flap-hybridizing sequence, wherein hybridization of a second cassette-specific invasive oligonucleotide to the second cleaved flap-hybridizing sequence of the second FRET cassette oligonucleotide forms an invasive cleavage structure cleavable by a FEN-1 endonuclease at a cleavage site between the second fluorophore moiety and the third quencher moiety, and wherein cleavage of the second FRET cassette oligonucleotide at the cleavage site produces a cassette cleavage product comprising the second fluorophore moiety.

Embodiment 10 is the composition of embodiment 9, wherein the second FRET cassette oligonucleotide is a second 5' flap FRET cassette comprising a 5' flap portion, wherein the cassette cleavage product is a second cassette cleaved flap comprising the second fluorophore, and wherein the composition further comprises: (iv) a second masking oligonucleotide comprising a fourth quencher moiety, wherein at least a portion of the second masking oligonucleotide is specifically hybridizable to the 5' flap portion of the second FRET cassette oligonucleotide, wherein hybridization of the second masking oligonucleotide to the second cassette cleaved flap forms a second duplex having a second melting temperature that is higher than the first melting temperature, and wherein fluorescence emission from the second fluorophore moiety in the second duplex is quenched by the fourth quencher moiety.

Embodiment 11 is the composition of embodiment 9, wherein the second cassette cleavage product comprises no more than 5, preferably no more than 4, preferably no more than 3, preferably no more than 2 nucleotides.

Embodiment 12 is the composition of any one of embodiments 9 to 11, wherein emission signals from the first fluorophore moiety and the second fluorophore moiety are detectable in the same fluorescence detection channel of a fluorescence-monitoring apparatus.

Embodiment 13 is the composition of any one of embodiments 9 to 12, wherein the first fluorophore moiety and the second fluorophore moiety are the same as each other.

Embodiment 14 is the composition of any one of embodiments 9 to 12, wherein the first fluorophore moiety and the second fluorophore moiety are not the same as each other.

Embodiment 15 is the composition of any one of embodiments 10 and 12 to 14, wherein the third quencher moiety and the fourth quencher moiety are the same as each other.

Embodiment 16 is a method of determining which of two different FRET cassettes in a reaction mixture cleaved to generate a fluorescent signal, the method comprising the steps of: (a) performing a multiplex invasive cleavage reaction in the reaction mixture to cleave one or both of a first FRET cassette and a second FRET cassette to produce two different fluorescent cleavage products, if cleavage occurred, the first FRET cassette comprising a first 5' flap portion having a fluorophore attached thereto, attachment of the fluorophore being arranged so that cleavage of the first FRET cassette by a FEN-1 endonuclease in the multiplex invasive cleavage reaction produces a first cassette cleaved flap comprising the fluorophore, the reaction mixture comprising a first masking oligonucleotide that stably hybridizes to the first cassette cleaved flap to form a first duplex at a temperature below a first Tm, but not at a temperature above the first Tm, wherein fluorescence emission from the fluorophore of the first cassette cleaved flap of the first duplex is quenched, and each of the two different fluorescent cleavage products produced in the multiplex invasive cleavage reaction being characterized by different temperature-dependent fluorescence quenching profiles in the reaction mixture; (b) measuring fluorescent signal produced in the reaction mixture using a single channel of a fluorescence monitoring apparatus under temperature conditions that differentially quench fluorescence produced by the different fluorescent cleavage products of the multiplex invasive cleavage reaction; and (c) determining from the results of step (b) which of the different FRET cassettes was cleaved in the multiplex invasive cleavage reaction.

Embodiment 17 is the method of embodiment 16, wherein the second FRET cassette in step (a), if cleaved, produces a fluorescent cleavage product that does not hybridize to any masking oligo in the reaction mixture to result in fluorescence quenching.

Embodiment 18 is the method of embodiment 17, wherein step (c) comprises comparing fluorescent signals measured at the temperature below the first Tm and the temperature above the first Tm.

Embodiment 19 is the method of embodiment 18, wherein step (c) comprises comparing fluorescent signals by calculating differences between measured fluorescent signals.

Embodiment 20 is the method of embodiment 17, wherein step (b) comprises measuring any of the fluorescent signal at the temperature below the first Tm, where fluorescence emission from the fluorophore of the first cassette cleaved flap of the first duplex is quenched, and wherein step (c) comprises determining that the second FRET cassette cleaved in the reaction mixture if measurable fluorescence was detected in step (b).

Embodiment 21 is the method of embodiment 17, wherein step (b) comprises measuring any of the fluorescent signal at each of the temperature below the first Tm and the temperature above the first Tm, and wherein step (c) comprises determining that the first FRET cassette cleaved in the reaction mixture if the fluorescent signal measured at the temperature above the first Tm is greater than the fluorescent signal measured at the temperature below the first Tm.

Embodiment 22 is the method of any one of embodiments 16 to 21, wherein step (b) comprises measuring any of the fluorescent signal produced in the reaction mixture as a function of temperature to generate a melting/annealing curve.

Embodiment 23 is the method of embodiment 22, wherein step (c) comprises calculating a derivative of the melting/annealing curve, and then determining from the calculated derivative whether the reaction mixture comprises the first duplex characterized by the first Tm as an indicator that the first FRET cassette cleaved in the reaction mixture.

Embodiment 24 is the method of embodiment 16, wherein the second FRET cassette comprises a second 5' flap sequence having a fluorophore attached thereto, attachment of the fluorophore being arranged so that cleavage of the second FRET cassette by the FEN-1 endonuclease in the multiplex invasive cleavage reaction produces a second cassette cleaved flap comprising the fluorophore, wherein the reaction mixture comprises a second masking oligo that hybridizes to the second cassette cleaved flap to form a second duplex at a temperature below a second Tm, but not at a temperature above the second Tm, wherein fluorescence emission from the fluorophore of the second cassette cleaved flap of the second duplex is quenched, and wherein the first Tm and the second Tm differ by at least 5° C.

Embodiment 25 is the method of embodiment 24, wherein the first Tm is greater than the second Tm, wherein step (b) comprises measuring any of the fluorescent signal at the temperature below the second Tm and at the temperature above the first Tm, and wherein step (c) comprises determining that at least one of the first FRET cassette and the second FRET cassette cleaved in the reaction mixture if the fluorescent signal measured at the temperature above the first Tm is greater than the fluorescent signal measured at the temperature below the second Tm.

Embodiment 26 is the method of either embodiment 24 or 25, wherein step (b) comprises measuring any of the fluorescent signal produced in the reaction mixture as a function of temperature to generate a melting/annealing curve.

Embodiment 27 is the method of embodiment 26, wherein step (c) comprises calculating a derivative of the melting/annealing curve, and then determining from the calculated derivative whether the reaction mixture comprises the first duplex characterized by the first Tm as an indicator that the first FRET cassette cleaved in the reaction mixture.

Embodiment 28 is the method of embodiment 26, wherein step (c) comprises calculating a derivative of the melting/annealing curve, and then determining from the calculated derivative whether the reaction mixture comprises the second duplex characterized by the second Tm as an indicator that the second FRET cassette cleaved in the reaction mixture.

Embodiment 29 is the method of any one of embodiments 16 to 28, wherein the first and second FRET cassettes are labeled with identical fluorophores.

Embodiment 30 is the method of any one of embodiments 16 to 28, wherein the first and second FRET cassettes are not labeled with identical fluorophores.

Embodiment 31 is the method of any one of embodiments 16 to 30, wherein the FEN-1 endonuclease of the multiplex invasive cleavage reaction in step (a) comprises a thermostable FEN-1 endonuclease.

Embodiment 32 is the method of any one of embodiments 16 to 31, wherein step (c) comprises determining with a computer programmed with software.

Embodiment 33 is a method of analyzing a sample comprising target nucleic acids, the method comprising the steps of: (a) contacting, in a reaction mixture, any of a first target nucleic acid of the sample with a first primary probe oligonucleotide comprising a sequence complementary thereto, and a FEN-1 endonuclease under conditions such that if the first primary probe oligonucleotide is hybridized to the first target nucleic acid, the first primary probe is cleaved by the FEN-1 endonuclease to generate a first primary cleaved flap, wherein the first primary cleaved flap hybridizes to the cleaved flap-hybridizing sequence of a first FRET cassette oligonucleotide contained in the reaction mixture to form an invasive cleavage structure that is cleaved by the FEN-1 endonuclease at a cleavage site between a first fluorophore moiety and a first quencher moiety of the first FRET cassette oligonucleotide to release a first cassette cleaved flap comprising the first fluorophore moiety, wherein a first masking oligonucleotide comprising a second quencher moiety hybridizes to the first cassette cleaved flap to form a duplex at a temperature that is below a first Tm of the first masking oligonucleotide and the first cassette cleaved flap, wherein fluorescence emission from the first fluorophore moiety of the duplex is quenched by the second quencher moiety, and wherein at a second temperature that is above the first Tm, the first masking oligonucleotide and the first cassette cleaved flap do not form a stable duplex; (b) detecting any fluorescence emitted from the first fluorophore moiety at the second temperature; and (c) determining either that the sample comprises the first target nucleic acid if fluorescence emitted from the first fluorophore moiety is detected in step (b), or the sample does not comprise the first target nucleic acid if fluorescence emitted from the first fluorophore moiety is not detected in step (b).

Embodiment 34 is the method of embodiment 33, wherein step (a) further comprises contacting, in the reaction mixture, any of a second target nucleic acid of the sample with a second primary probe oligonucleotide comprising a sequence complementary thereto, and the FEN-1 endonuclease under conditions such that if the second primary probe oligonucleotide hybridizes to the second target nucleic acid, the second primary probe is cleaved by the FEN-1 endonuclease to generate a second primary cleaved flap that is different from the first primary cleaved flap, wherein the second primary cleaved flap hybridizes to the cleaved flap-hybridizing sequence of a second FRET cassette oligonucleotide contained in the reaction mixture to form an invasive cleavage structure that is cleaved by the FEN-1 endonuclease at a cleavage site between a second fluorophore moiety and a third quencher moiety of the second FRET cassette oligonucleotide to release a second cassette cleaved flap comprising the second fluorophore moiety, wherein at a third temperature that is below a second Tm, a second masking oligonucleotide comprising a fourth quencher moiety hybridizes to the second cassette cleaved flap to form a duplex, wherein fluorescence emission from the second fluorophore moiety of the duplex is quenched by the fourth quencher moiety, wherein at a fourth temperature that is above the second Tm, the second masking oligonucleotide and the second cassette cleaved flap do not form a stable duplex, and wherein the first Tm and the second Tm differ from each other by at least 5° C.; wherein step (b) further comprises detecting any fluorescence emitted from the second fluorophore moiety at the fourth temperature; and wherein step (c) further comprises determining either that the sample comprises the second target nucleic acid if fluorescence emitted from the second fluorophore moiety of the 5' flap cleavage product of the second FRET cassette oligonucleotide is detected in step (b), or the sample does not comprise the first target nucleic acid if fluorescence emitted from the second fluorophore moiety of the 5' flap cleavage product of the second FRET cassette oligonucleotide is not detected in step (b).

Embodiment 35 is the method of embodiment 33, wherein step (a) further comprises contacting, in the reaction mixture, any of a second target nucleic acid of the sample with a second primary probe oligonucleotide comprising a sequence complementary thereto, and the FEN-1 endonuclease under conditions such that if the second primary probe oligonucleotide hybridizes to the second target nucleic acid, the second primary probe is cleaved by the FEN-1 endonuclease to generate a second primary cleaved flap, wherein the second primary cleaved flap hybridizes to the cleaved flap-hybridizing sequence of a second FRET cassette oligonucleotide contained in the reaction mixture to form an invasive cleavage structure that is cleaved by the FEN-1 endonuclease at a cleavage site between a second fluorophore moiety and a third quencher moiety of the second FRET cassette oligonucleotide to release a cleavage product comprising the second fluorophore moiety, wherein the cleavage product does not hybridize to any masking oligonucleotide in the reaction mixture to result in fluorescence quenching; wherein step (b) further comprises detecting any fluorescence emitted from the second fluorophore moiety of the cleavage product; and wherein step (c) further comprises determining either that the sample comprises the second target nucleic acid if fluorescence emitted from the second fluorophore moiety is detected in step (b), or the sample does not comprise the first target nucleic acid if fluorescence emitted from the second fluorophore moiety is not detected in step (b).

Embodiment 36 is the method of either embodiment 34 or embodiment 35, wherein step (b) comprises detecting with a single channel of a fluorescence monitoring device any fluorescence emitted from the first and second fluorophore moieties.

Embodiment 37 is the method of embodiment 36, wherein step (b) is performed while a nucleic acid amplification reaction is occurring in the reaction mixture, and wherein products of the nucleic acid amplification reaction comprise the first target nucleic acid and the second target nucleic acid.

Embodiment 38 is the method of embodiment 37, wherein the nucleic acid amplification reaction comprises steps for thermocycling, and wherein the reaction mixture further comprises a thermostable DNA polymerase.

Embodiment 39 is the method of any one of embodiments 33 to 36, wherein step (b) is performed as the temperature of the reaction mixture decreases to permit annealing of masking oligonucleotides and complementary cassette cleaved flaps.

Embodiment 40 is the method of 36, wherein the first and second fluorophore moieties are the same as each other.

Embodiment 41 is the method of embodiment 36, wherein the step of (b) detecting any fluorescence comprises measuring any fluorescence.

Embodiment 42 is the method of embodiment 41, further comprising the step of either detecting or measuring fluorescence at the first temperature.

Embodiment 43 is the method of any one of embodiments 34 or 35, wherein the first fluorophore moiety and the second fluorophore moiety are both detectable in the same fluorescence detection channel of an energy sensor device.

Embodiment 44 is the method of embodiment 43, wherein the second fluorophore moiety is the same as the first fluorophore moiety.

Embodiment 45 is the method of embodiment 43, wherein the second fluorophore moiety is not the same as the first fluorophore moiety.

Embodiment 46 is the method of any one of embodiments 33 to 43, wherein fluorescence from the second fluorophore is detected and/or measured at the first temperature.

Embodiment 47 is the method of any one of embodiments 33 to 44, wherein the third quencher moiety is the same as the first quencher moiety and/or the second quencher moiety.

Embodiment 48 is the method of any one of embodiments 33 to 47, wherein the reaction mixture comprises primer oligonucleotides that amplify target nucleic acids, wherein at least one primer oligonucleotide acts as an invasive oligonucleotide in the presence of a primary probe oligonucleotide and target nucleic acid and/or target amplicon to form an invasive cleavage structure that is cleaved by the thermostable FEN-1 endonuclease.

Embodiment 49 is the method of any one of embodiments 33 to 48, wherein step (c) comprises determining with a computer programmed with software.

Embodiment 50 is a system for determining which among a plurality of target nucleic acid analytes is present in a reaction mixture, where each target nucleic acid analyte of the plurality is detectable by a fluorescent signal, the system comprising: a thermocycler; a fluorometer in optical communication with the thermocycler, wherein the fluorometer measures, with a single optical channel, fluorescent signal indicating production of nucleic acid amplification products by the thermocycler; and a computer in communication with the fluorometer, wherein the computer is programmed with software instructions causing the computer to: (a) obtain a melting/annealing curve data set prepared from measurements made by the fluorometer, (b) determine that a first target nucleic acid is present in the reaction mixture by detecting a fluorescent signal from a first fluorescent cleavage product in the melting/annealing curve data set at a temperature where fluorescence in the reaction mixture is maximally quenched, (c) prepare a derivative plot from the melting/annealing curve data set, and (d) determine that a second target nucleic acid is present in the reaction mixture if the derivative plot comprises a feature characteristic of a first duplex, wherein the first duplex comprises a first masking oligonucleotide, and a second fluorescent cleavage product produced in the reaction mixture when the second target nucleic acid is present.

Embodiment 51 is the system of embodiment 50, wherein the computer is further programmed with software instructions causing the computer to: (e) determine that a third target nucleic acid is present in the reaction mixture if the derivative plot comprises a feature characteristic of a second duplex, wherein the second duplex comprises a second masking oligonucleotide and a third fluorescent cleavage product produced in the reaction mixture when the third target nucleic acid is present.

Embodiment 52 is the system of either embodiment 50 or embodiment 51, wherein the feature characteristic of the first duplex comprises the maximum, minimum, or zero crossing point of a calculated derivative.

Embodiment 53 is the system of embodiment 52, wherein the calculated derivative comprises a calculated first derivative, wherein the feature characteristic of the first duplex comprises as a first melting peak a first maximum of a calculated first derivative of the melting/annealing curve data set, and wherein the feature characteristic of the second duplex comprises as a second melting peak a second maximum of the calculated first derivative of the melting/annealing curve data set.

Embodiment 54 is the system of any one of embodiments 50 to 53, wherein the thermocycler, the fluorometer, and the computer are all components of a real-time PCR instrument.

Embodiment 55 is the system of embodiment 50, wherein the melting/annealing curve data set obtained by the computer comprises data points indicating fluorescence as a function of temperature.

BRIEF DESCRIPTION OF THE DRAWINGS

FIG. 2A presents the structure of an example "5' flap FRET cassette" (SEQ ID NO:7). FIG. 2B presents an example "5' flap FRET cassette 1" (SEQ ID NO:7) hybridized to a "cleaved flap from primary probe" (SEQ ID NO:8) (i.e., the primary cleaved flap serving as an invasive oligonucleotide). FIG. 2C illustrates temperature-dependent interaction between a "cassette cleaved flap" (SEQ ID NO:9) (i.e., a 5' flap cleaved from a 5' flap FRET cassette) and a complementary "masking oligo" (SEQ ID NO:10).

FIGS. 7A-7D provide a collection of graphs showing fluorescence measured in the HEX™ dye channel as a function of cycle number and of the temperature at which the fluorescent measurement was made. FIGS. 7A and 7B show results obtained for reactions that included target Analyte B only (using a 5' flap FRET cassette and masking oligonucleotide that quenches at low temperature) when fluorescence was measured at 63° C. and 39° C., respectively. FIGS. 7C and 7D show results obtained for reactions that included target Analytes A and B together, with detection of Analyte A using a flapless FRET cassette (does not include a 5' flap) and producing a product that fluoresces at both temperatures, where fluorescence was measured at 63° C. and 39° C., respectively. Procedures are described in Example 3.

DEFINITIONS

Figure 1:
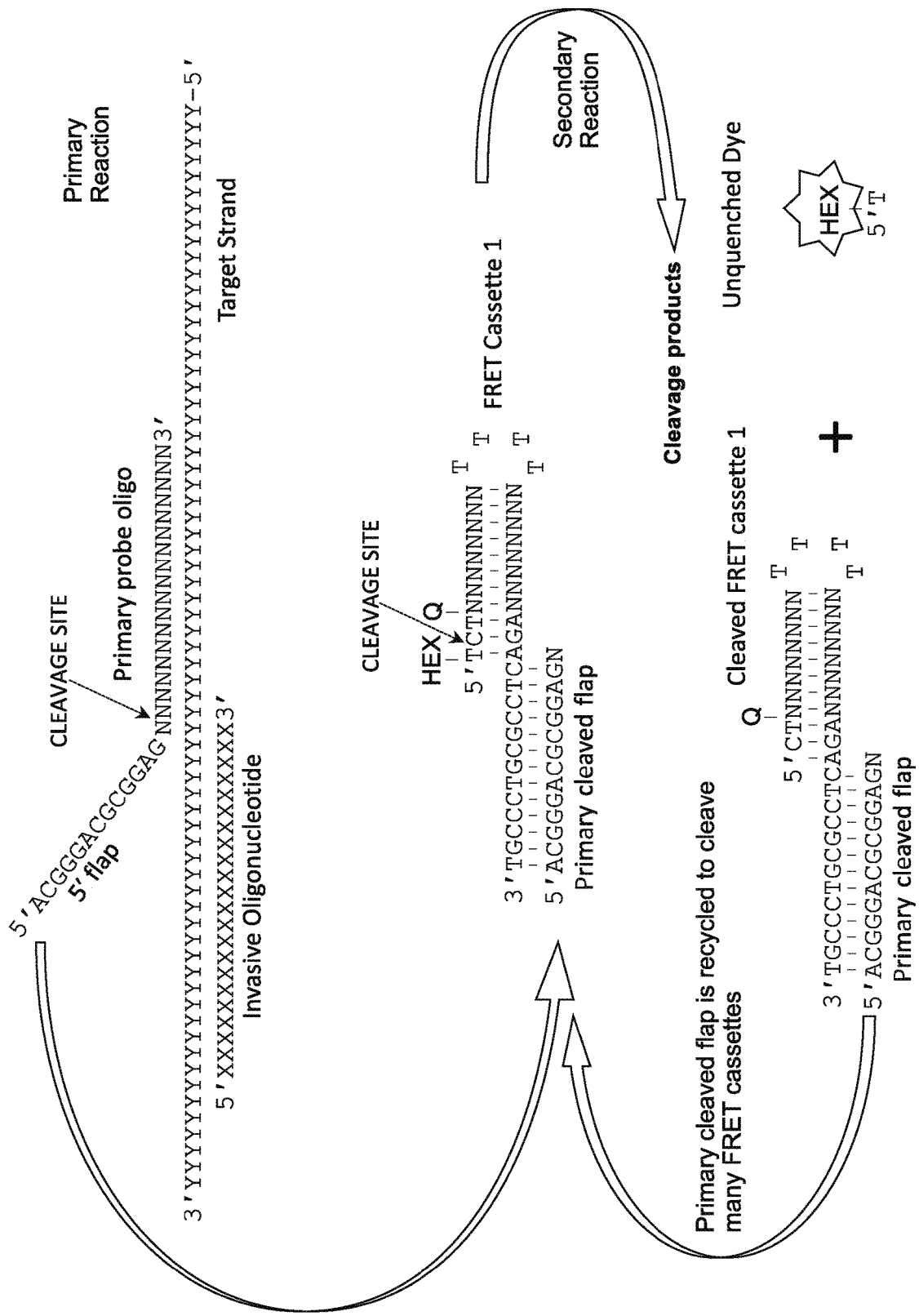
FIG. 1 provides a schematic diagram of an assay employing two invasive cleavage reactions conducted in a serial fashion in the same reaction mixture. In the primary reaction, an "invasive oligonucleotide" (SEQ ID NO:1) and a "primary probe oligo" (SEQ ID NO:2) (i.e., a 5' flap oligonucleotide) hybridize to a "target strand" nucleic acid (SEQ ID NO:3) to form an invasive cleavage structure cleavable by a FEN-1 endonuclease to release a cleaved 5' flap ("primary cleaved flap") (SEQ ID NO:4). In a secondary reaction, the primary cleaved flap from the primary reaction hybridizes to a FRET cassette ("FRET cassette 1") (SEQ ID NO:5), a hairpin oligonucleotide labeled with a fluorescent dye and a quencher molecule, to form a second invasive cleavage structure that is cleavable by a FEN-1 endonuclease at a site between the hexachlorofluorescein (HEX™ dye) fluorophore (shown as "HEX") and the quencher ("Q"). Cleavage of "FRET cassette 1" (SEQ ID NO:5) produces "cleaved FRET cassette 1" (SEQ ID NO:6) and separates the quencher from the fluorophore, such that fluorescence signal from the fluorophore can be detected. Each primary cleaved flap can hybridize to a succession of new uncleaved FRET cassettes to form additional fluorescent cleavage products.

To facilitate an understanding of the present disclosure, a number of terms and phrases are defined below. Additional definitions are set forth throughout the detailed description. Throughout the specification and claims, the following terms take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition (i.e., a composition "consisting of" the recited components). As used herein, the term "sample" refers to a specimen that may contain an analyte of interest (e.g., microbe, virus, nucleic acid such as a gene, or components thereof, which includes nucleic acid sequences in or derived from an analyte). Samples may be from any source, such as biological specimens or environmental sources. Biological specimens include any tissue or material derived from a living or dead organism that may contain an analyte or nucleic acid in or derived from an analyte. Examples of biological samples include: nasal swab samples, vaginal swab samples, respiratory tissue, exudates (e.g., bronchoalveolar lavage), biopsy, sputum, peripheral blood, plasma, serum, lymph node, gastrointestinal tissue, feces, urine, or other fluids, tissues or materials. Examples of environmental samples include water, ice, soil, slurries, debris, biofilms, airborne particles, and aerosols. Samples may be processed specimens or materials, such as obtained from treating a sample by using filtration, centrifugation, sedimentation, or adherence to a medium, such as matrix or support. Other processing of samples may include treatments to physically or mechanically disrupt tissue, cellular aggregates, or cells to release intracellular components that include nucleic acids into a solution which may contain other components, such as enzymes, buffers, salts, detergents, and the like. Samples being tested for the presence of an analyte may sometimes be referred to as "test samples."

The terms "target nucleic acid" and "target sequence," refer to a nucleic acid that is to be detected or analyzed. Thus, a "target" nucleic acid is sought to be distinguished from other nucleic acids or nucleic acid sequences. For example, when used in reference to an amplification reaction, these terms may refer to the nucleic acid or portion of nucleic acid that will be amplified by the reaction, when used in reference to a polymorphism, they may refer to the locus in a nucleic acid of a suspected polymorphism. When used in reference to an invasive cleavage reaction, these terms typically refer to a nucleic acid molecule containing a sequence that selectively hybridizes to a first nucleic acid molecule (e.g. a probe oligonucleotide) and a second nucleic acid molecule (an invasive oligonucleotide) to form an overlapping invasive cleavage structure. Generally, the target nucleic acid (e.g., present within, isolated from, enriched from, or amplified from or within a sample) is located within a target region and is identifiable via the successful formation of an invasive cleavage structure in combination with the first and second nucleic acid molecules (e.g., probe oligonucleotide and invasive oligonucleotide) that is cleavable by a cleavage agent. Target nucleic acids from an organism are not limited to genomic DNA and RNA. Target nucleic acids from an organism may comprise any nucleic acid species, including but not limited to genomic DNAs and RNAs, messenger RNAs, structural RNAs, ribosomal and tRNAs, and small RNAs such as snRNAs, siRNAs and microRNAs (miRNAs). See, e.g., U.S. Pat. No. 7,851,150, which is incorporated herein by reference in its entirety. A "segment" is defined as a region of nucleic acid within the target sequence.

Because mononucleotides are reacted to make oligonucleotides in a manner such that the 5' phosphate joined to one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

As used herein the term "5' terminal portion" refers to a portion of nucleic acid having a 5' terminus (i.e., a 5' end for which the 5' phosphate is not linked to the 3' oxygen of a mononucleotide pentose ring). The term "3' terminal portion" refers to a portion of nucleic acid having a 3' terminus (i.e., a 3' end for which the 3' oxygen is not linked to the 5' phosphate of a subsequent mononucleotide pentose ring).

As used herein, the terms "hybridization" or "hybridize" (and grammatical equivalents) are used in reference to the pairing of complementary nucleic acids. Hybridization and the strength of hybridization (i.e., the strength of the association between the nucleic acid strands participating in a duplex) is impacted by factors such as the degree of complementary between the nucleic acids, stringency of the conditions involved, the $T_m$ of the formed hybrid, and the G:C ratio within the nucleic acids.

When two different, non-overlapping oligonucleotides anneal to different regions of the same linear complementary nucleic acid, and the 3' end of one oligonucleotide is adjacent to the 5' end of the other, the former may be called the "upstream" oligonucleotide and the latter the "downstream" oligonucleotide. Similarly, when two overlapping oligonucleotides are hybridized to the same linear complementary nucleic acid, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, the term "Tm" is used in reference to the "melting temperature" of a nucleic acid strand with respect to a complementary nucleic acid strand. The melting temperature of nucleic acid duplex is the temperature at which a population of double-stranded nucleic acid molecules becomes half dissociated into single strands. Measuring the melting temperature of a labeled nucleic acid duplex typically comprises plotting fluorescence as a function of temperature to produce a melting curve that is characteristic of the dissociation of the duplex. When the negative first derivative of a melting curve is graphed as a function of temperature, the $T_m$ is identifiable as a peak. See, e.g., K M Ririe, et al., Analytical Biochemistry 245:154-160 (1997).

A "calculated $T_m$" refers to a melting temperature determined by calculation from the physical sequence of complementary nucleic acids, along with factors of reaction conditions (e.g., salt concentration, concentrations of the complementary strands in a mixture). Several equations for calculating the $T_m$ of nucleic acids are well known in the art. As indicated by standard references, a simple estimate of the $T_m$ value may be calculated by the equation: $T_m=81.5+0.41(\% G+C)$, when a nucleic acid is in aqueous solution at 1 M NaCl (See, e.g., Young and Anderson, (1985) in *Nucleic Acid Hybridisation: A Practical Approach* (Hames & Higgins, Eds.) pp 47-71, IRL Press, Oxford). Other computations for calculating $T_m$ are known in the art and take structural and environmental, as well as sequence characteristics into account (See, e.g., Allawi, H. T. and SantaLucia, J., Jr. Biochemistry 36, 10581-94 (1997)); and Santa-Lucia, Proc Natl Acad Sci USA., 95(4):1460 (1998)).

As used herein, the term "cycling hybridization" refers to a condition in which incubation of a reaction mixture comprising nucleic acids at or near (e.g., within 4° C., more preferably within 3° C., still more preferably within 2° C., and yet still more preferably within 1° C.) the $T_m$ of hybridized nucleic acid strands (e.g., probe oligonucleotides and their complementary target nucleic acids) such that the oligonucleotides constantly anneal and disassociate from the target strands without temperature cycling (i.e., without shifting the temperature of the reaction mixture to alternately melt and anneal the probe-target nucleic acid duplexes).

As used herein, an "invasive cleavage assay" is a procedure that detects or quantifies a target nucleic acid by enzymatic cleavage of one or more different invasive cleavage structures, where at least one of the cleavage structures includes a FRET cassette. In preferred embodiments, the invasive cleavage assay combines two invasive signal amplification reactions (e.g., a "primary reaction" and a "secondary reaction") in series in a single reaction mixture. Reagents for an invasive cleavage assay can include: a structure-specific 5' nuclease (e.g., a FEN-1 endonuclease), an "invasive oligonucleotide," a "primary probe," and a "FRET cassette."

As used herein, the term "INVADER assay" refers to a structure-specific flap endonuclease cleavage assay (Hologic, Inc.) and is described, e.g., in U.S. Pat. Nos. 5,846, 717; 5,985,557; 5,994,069; 6,001,567; 6,090,543; 6,872, 816; 7,935,800; 9,133,503; 9,096,893, Lyamichev et al., *Nat. Biotech.*, 17:292 (1999), Hall et al., *Proc. Natl. Acad. Sci. USA*, 97:8272 (2000), Allawi, et al., *RNA* (2004), 10:1153-1161 (2004), each of which is herein incorporated by reference in its entirety for all purposes.

The term "invasive cleavage structure" (sometimes simply "cleavage structure") as used herein refers to an overlapping nucleic acid duplex structure that is a substrate for cleavage by a flap endonuclease (e.g., a FEN-1 endonuclease). The cleavage reaction catalyzed by the enzyme does not require extension of any nucleic acid strand. In some embodiments an invasive cleavage structure comprises: (i) a continuous nucleic acid strand (e.g., a target DNA or RNA); (ii) an upstream nucleic acid (e.g., an invasive oligonucleotide, sometimes referred to as an INVADER oligonucleotide) that hybridizes to a first portion of the target strand to form an upstream duplex; and (iii) a downstream nucleic acid (e.g., a 5' flap probe, or a primary probe oligonucleotide having a 5' flap that is not complementary to the target strand) that hybridizes to form a downstream duplex. The upstream and downstream nucleic acids anneal to contiguous regions of the target nucleic acid, and where an overlap forms between the 3' portion of the upstream nucleic acid and the duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary to the target nucleic acid, and whether or not those bases are natural bases or non-natural bases. In some embodiments, the 3' portion of the upstream nucleic acid that overlaps with the downstream duplex is a non-base chemical moiety such as an aromatic ring structure (e.g., as disclosed, for example, in U.S. Pat. No. 6,090,543, incorporated herein by reference in its entirety). In some embodiments, one or more of the nucleic acids may be attached to each other through a covalent linkage such as nucleic acid stem-loop, or through a non-nucleic acid chemical linkage (e.g., a multi-carbon chain). An invasive cleavage structure also is created when a cleaved 5' flap hybridizes to a FRET cassette (e.g., wherein the "target nucleic acid" and the "downstream nucleic acid" are covalently linked in a stem-loop configuration). The "target nucleic acid" sequence of a FRET cassette that hybridizes to a cleaved 5' flap can be referred to as a "cleaved flap-hybridizing sequence."

In some embodiments, target nucleic acid is amplified (e.g., by PCR), and amplification products are detected using an invasive cleavage assay as the amplification reaction is occurring. Assays configured for performing a detection assay (e.g., invasive cleavage assay) in combination with an amplification assay are described in U.S. Pat. No. 9,096,893, incorporated herein by reference in its entirety for all purposes. In further embodiments, RNA target nucleic acids may be reverse-transcribed, amplified, and detected using an invasive cleavage assay in a single reaction, as described in WO 2006/050499, incorporated herein by reference in its entirety for all purposes.

As used herein, the term "probe oligonucleotide," refers to an oligonucleotide that interacts with a target nucleic acid to form a detectable complex. In some embodiments, the complex between a probe and target is detected while it exists. In other embodiments, the formation of the complex may be detected when it no longer exits (e.g., by detection of an event, such as a cleavage event, that occurred as a result of formation of the probe/target complex).

As used herein, the term "flap probe" refers to a probe oligonucleotide that comprises a target-specific portion that specifically hybridizes to a target nucleic acid, and a 5' flap portion that does not hybridize to the target nucleic acid. Typically, the 5' flap portion is not complementary to the region of the target nucleic acid adjacent to the duplex formed between the target nucleic acid and the target-specific portion of the flap probe.

As used herein in reference to a serial invasive cleavage assay, a "primary probe" is a flap probe comprising a 3' sequence or portion complementary to a target nucleic acid that is to be detected, and 5' flap portion that is not complementary to the target nucleic acid (i.e., the 5' flap portion that is not complementary does not hybridize to the target nucleic acid). The 5' flap portion is configured such that, upon cleavage of the primary probe participating in an invasive cleavage structure in a "primary" reaction of a sequential invasive cleavage assay, the cleaved 5' flap released from the primary probe can hybridize to a FRET cassette to promote a secondary reaction of the sequential invasive cleavage assay.

As used herein, the term "primary reaction" generally refers to flap endonuclease cleavage of a primary probe, whereby a cleaved 5' flap is generated. When a primary probe is cleaved with a FEN-1 endonuclease, the sequence of the cleaved 5' flap from a primary probe will typically be the 5' flap portion of the primary probe, plus the first (5'-most) nucleotide of the target-specific portion of the primary probe.

As used herein, the term "secondary reaction" generally refers to hybridization of a cleaved 5' flap from a primary reaction to a FRET cassette to form a secondary invasive cleavage structure, and cleavage of the secondary invasive cleavage structure by a flap endonuclease to produce a detectable signal.

As used herein, a reaction is "active" when reaction products are generated. For example, a secondary reaction is active when a reaction mixture containing necessary components (e.g., including a FRET cassette, a cleaved 5' flap specific for the FRET cassette, and a FEN enzyme) are incubated at a temperature that permits cycling hybridization of the cleaved 5' flap to FRET cassettes in the reaction mixture to result in cleavage of the FRET cassettes and separation of donor (e.g., fluorophore) and acceptor (e.g., quencher) moieties.

The term "invasive oligonucleotide" (sometimes "INVADER oligonucleotide") refers to an oligonucleotide that hybridizes to a target nucleic acid at a location near the region of hybridization between a probe and the target nucleic acid, wherein the invasive oligonucleotide comprises a portion (e.g., a chemical moiety, or nucleotide, whether complementary to that target or not) that overlaps with the region of hybridization between the probe and target. In some embodiments, the invasive oligonucleotide contains a sequence at its 3' end that is substantially the same as a sequence located at the 5' end of a probe oligonucleotide.

As used herein, the term "FRET" refers to fluorescence resonance energy transfer, a process in which chemical moieties (e.g., fluorophores) transfer energy among themselves, or from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a quenching molecule). FRET is known to those of skill in the art and has been described (See Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FRET cassette" refers to an oligonucleotide comprising a stem-loop or hairpin structure (i.e., a region of a nucleic acid base paired intramolecularly to form a double helix stem having a loop of nucleotides connecting the base paired strands on one end of the stem), that includes a donor moiety (e.g., a "fluorophore") and a nearby acceptor moiety (e.g., a "quencher"), where attachment of the donor and acceptor moieties to the same FRET cassette substantially suppresses (e.g., quenches) a detectable energy emission from the donor moiety (e.g., a fluorescent emission). FEN-1 enzymes catalyze hydrolytic cleavage of the phosphodiester bond 3' adjacent to the junction of single and double stranded DNA, generally one nucleotide into the 5' end of the stem-loop portion of the oligonucleotide, releasing the 5' nucleotide or 5' flap from the stem-loop portion of the FRET cassette. The fluorophore moiety is typically attached to the FRET cassette oligonucleotide at a 5' terminus or in a 5' flap, while the quencher moiety is typically attached to the stem-loop portion of the oligonucleotide.

The "cleaved flap-hybridizing sequence" of a FRET cassette refers to the nucleotide base sequence of the 3' portion of the FRET cassette that specifically hybridizes to the 3' end of a complementary nucleic acid or oligonucleotide, e.g., a 5' flap cleaved from a primary probe (a "primary cleaved flap"), with the 3' terminus of the complementary oligonucleotide positioned to form an invasive cleavage structure (i.e., the substrate for a FEN enzyme) when the flap cleavage product is hybridized to the FRET cassette, such that the cleavage site on the FRET cassette is positioned between the fluorophore moiety and the quencher moiety.

As used herein, the term "5' flap FRET cassette" refers to a FRET cassette oligonucleotide that has a single stranded 5' flap portion, a stem-loop portion, and a single-stranded 3' portion comprising the cleaved flap-hybridizing sequence, and wherein the 5' flap portion and the cleaved flap-hybridizing sequence are not complementary to each other.

As used herein, the term "flapless FRET cassette" refers to a FRET cassette that does not have a single-stranded 5' portion, e.g., one or more non-complementary 5' nucleotides, and wherein the 5' terminal nucleotide of the oligonucleotide is base pairable as the last base pair on the non-loop end of the stem-loop portion of the FRET cassette Since amplification of the fluorescent signal from cleavage of FRET cassettes results from repeated or cycling hybridization of complementary oligonucleotides (e.g., a 5' flap cleaved from a primary probe) to the cleaved flap-hybridizing sequence of in a population of FRET cassettes, primary probes are typically designed such that the cleaved 5' flap is not extendable by a polymerase using the FRET cassette as a template. For example, primary probes are typically designed to produce a 5' cleaved flap product that, when hybridized to a FRET cassette, has a 3' terminus that is not complementary to the cleaved flap-hybridizing sequence in the FRET cassette.

In some embodiments, a mixture of FRET cassettes having two or more different cleaved flap-hybridizing sequences may be used (e.g., in a multiplex invasive cleavage reaction). Two cleaved flap-hybridizing sequences are said to be "different" from each other when a cleaved flap product is hybridizable to one cleaved flap-hybridizing sequence is not measurably hybridizable (e.g., under invasive cleavage assay conditions) to the other cleaved flap-hybridizing sequence, and vice versa. Cleavage of the FRET cassette by a FEN enzyme (e.g., a FEN-1 endonuclease) in a secondary reaction separates the donor and acceptor moieties with the result of relieving the suppression and permitting generation of a signal. In some embodiments, the donor and acceptor moieties interact by fluorescence resonance energy transfer (e.g., "FRET"). In other embodiments, the donor and acceptor of the FRET cassette interact by a non-FRET mechanism.

As used herein, an "interactive" label pair refers to a donor moiety and an acceptor moiety being attached to the same FRET cassette, and being in energy transfer relationship (i.e., whether by a FRET or a non-FRET mechanism) with each other. A signal (e.g., a fluorescent signal) can be generated when the donor and acceptor moieties are separated, for example by cleavage of the FRET cassette in a secondary reaction. Different FRET cassettes that specifically hybridize to different cleaved 5' flaps can each include the same interactive label pair.

As used herein, the term "unlabeled" as used in reference to a probe oligonucleotide refers to a probe oligonucleotide that does not comprise any chromophore or fluorophore to facilitate detection. An unlabeled probe may comprise modifications, such as 3' blocking groups to prevent extension by a polymerase.

As used herein, the term "donor" refers to a moiety (e.g., a fluorophore) that absorbs at a first wavelength and emits at a second, longer wavelength. The term "acceptor" refers to a moiety such as a fluorophore, chromophore, or quencher and that is able to absorb some or most of the emitted energy from the donor when it is near the donor group (typically between 1-100 nm). An acceptor may have an absorption spectrum that overlaps the donor's emission spectrum. Generally, if the acceptor is a fluorophore, it then re-emits at a third, still longer wavelength. If the acceptor is a chromophore or quencher, it releases the energy absorbed from the donor without emitting a photon. In some preferred embodiments, alteration in energy levels of donor and/or acceptor moieties are detected (e.g., via measuring energy transfer between or from donors and/or acceptor moieties). This can involve detecting light emission. In some preferred embodiments, the emission spectrum of an acceptor moiety is distinct from the emission spectrum of a donor moiety such that emissions (e.g., of light and/or energy) from the moieties can be distinguished (e.g., spectrally resolved) from each other.

In some embodiments, a donor moiety is used in combination with multiple acceptor moieties. In a preferred embodiment, a donor moiety is used in combination with a non-fluorescing quencher moiety and with an acceptor moiety, such that when the donor moiety is close (e.g., between 1-100 nm, or more preferably, between 1-25 nm, or even more preferably around 10 nm or less) to the quencher, its excitation is transferred to the quencher moiety rather than the acceptor moiety, and when the quencher moiety is removed (e.g., by cleavage of a probe), donor moiety excitation is transferred to the acceptor moiety. In some preferred embodiments, emission from the acceptor moiety is detected (e.g., using wavelength shifting molecular beacons) (See Tyagi, et al., Nature Biotechnology 18:1191 (2000); Mhlanga and Malmberg, 2001 Methods 25, 463-471; Olivier, 2005 Mutant Res 573, 103-110, and U.S. Pat. App. 20030228703, each of which is incorporated herein by reference in its entirety).

As used herein, the term "distinct" in reference to signals (e.g., of one or more labels) refers to signals that can be differentiated one from another by, for example, spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the term "synthetic" as used in reference to a polynucleotide or oligonucleotide (e.g., a probe) refers to a nucleic acid created in a cell-free in vitro reaction (e.g., an enzymatic or chemical synthesis reaction). Examples of enzymatic formation of a synthetic nucleic acid include formation by restriction enzyme digestion, polymerization (templated or non-templated), ligation, etc. Examples of chemical synthesis of nucleic acid include but are not limited to phosphodiester and phosphotriester chemistries, phosphoramidite and H-phosphonate, chemistries, etc. See e.g., *Methods in Molecular Biology, Vol 20: Protocols for Oligonucleotides and Analogs* pp. 165-189 (S. Agrawal, Ed., Humana Press, 1993).; *Oligonucleotides and Analogues: A Practical Approach*, pp. 87-108 (F. Eckstein, Ed., 1991); and Uhlmann and Peyman, supra. Agrawal and Iyer, Curr. Op. in Biotech. 6: 12 (1995); and *Anti-sense Research and Applications* (Crooke and Lebleu; Eds., CRC Press, Boca Raton, 1993), Beaucage and Caruthers, Tetrahedron Lett. 22: 1859-1862 (1981), and Agrawal and Zamecnik, U.S. Pat. No. 5,149,798 (1992). In some embodiments, pre-formed synthetic oligonucleotides are introduced into a reaction, while in other embodiments, synthetic oligonucleotides are formed or modified within a reaction (e.g., by action of a polymerase, ligase, cleavage enzyme, or the like).

As used herein, the term "flap endonuclease" or "FEN" (e.g., "FEN enzyme") refers to a class of nucleolytic enzymes that act as structure-specific endonucleases on DNA structures with a duplex containing a single-stranded 5' overhang, or 5' flap, on one of the strands that is displaced by another strand of nucleic acid, such that there are overlapping nucleotides at the junction between the single and double-stranded DNA. FEN enzymes catalyze hydrolytic cleavage of the phosphodiester bond 3' adjacent to the junction of single and double stranded DNA, releasing the overhang, or "flap" (see *Trends Biochem. Sci.* 23:331-336 (1998) and *Annu. Rev. Biochem.* 73: 589-615 (2004)). FEN enzymes may be individual enzymes or multi-subunit enzymes. In some particular embodiments, the FEN enzymatic activity may exist as an activity of another enzyme or protein complex, such as a DNA polymerase. In some preferred embodiments, the FEN enzyme does not possess a DNA polymerizing activity (e.g., does not polymerize DNA, even in the presence of template, a primer, and dNTPs). In other preferred embodiments, the FEN enzyme possesses a DNA polymerizing activity, but does not exhibit this activity by extending an oligo (e.g., a 5' flap cleaved from a primary probe, or deriving from another source) in a manner that substantially precludes cycling hybridization to the FRET cassette. For example, the FEN enzyme participating in a secondary invasive cleavage reaction to cleave a fluorophore or fluorescent 5' flap from a FRET cassette does not extend the cleaved 5' flap from the primary probe (i.e., the invasive probe that reversibly hybridizes to the FRET cassette to catalyze the cleavage reaction). A flap endonuclease may be thermostable. Examples of FEN enzymes useful in the methods disclosed herein are described in U.S. Pat. Nos. 5,614,402; 5,795,763; 6,090,606; and in published PCT applications identified by WO 98/23774; WO 02/070755; WO 01/90337; and WO 03/073067, each of which is incorporated by reference in its entirety. Particular examples of commercially available FEN enzymes include the CLEAV-ASE® enzymes (Hologic, Inc.).

As used herein, "FEN-1" refers to a non-polymerase flap endonuclease from a eukaryote or archaeal organism, as encoded by a FEN-1 (Flap Structure-Specific Endonuclease 1) gene. See, e.g., U.S. Pat. No. 6,562,611 to Kaiser, et al., and Kaiser M. W., et al. (1999) J. Biol. Chem., 274.21387; WO 02/070755, and U.S. Pat. No. 7,122,364, which are incorporated by reference herein in their entireties for all purposes. The term "FEN-1 activity" refers to any enzymatic activity of a FEN-1 enzyme. FEN-1 endonucleases also comprise modified FEN-1 proteins (e.g., chimerical proteins comprising portions of FEN-1 enzymes from different organisms), and enzymes comprising one or more mutations (e.g., substitutions, deletions, insertions, etc.), as described in WO 02/070755, and U.S. Pat. No. 7,122,364. An archaeal organism is any of the generally unicellular organisms of the biological kingdom Archaea.

References to "first" and "second" and "third" etc., (e.g., target nucleic acids, FRET cassettes, invasive cleavage assays, etc.) simply provide identifiers for distinguishing one from another, without necessarily indicating one precedes the other.

A "reaction mixture" is a combination of reagents (e.g., oligonucleotides, target nucleic acids, enzymes, etc.) in a single reaction vessel.

As used herein, a "multiplex" assay is a type of assay that detects or measures multiple analytes (two or more) in a single run of the assay. It is distinguished from procedures that measure one analyte per reaction mixture. A multiplex invasive cleavage assay is carried out by combining into a single reaction vessel the reagents for detecting or measuring two or more different analytes using independent invasive cleavage assays. In some embodiments, the same species of fluorescent reporter is detected in each of the assays of the multiplex. In other embodiments, different species of fluorescent reporter are used, but the different reporters are detectable in the same channel of an instrument that detects a range of fluorescent wavelengths.

The term "complementary," as used herein, refers to nucleobase sequences that are capable of forming a double-stranded, hydrogen bonded region. The nucleobase sequences may be "perfectly complementary" (i.e., each nucleobase in one sequence is capable of pairing with a corresponding nucleobase in a second sequence) or they may be "partially complementary" (i.e., at least one nucleobase in one sequence is incapable of hydrogen bonding with a corresponding nucleobase in a second sequence). The nucleobase sequences may be in the same or different polynucleotides.

The terms "duplex" and "hybrid duplex," as used herein, refer to a nucleic acid structure comprising a double-stranded, hydrogen-bonded region. Such structures may be fully or partially double-stranded and include RNA:RNA, RNA:DNA and DNA:DNA molecules and analogs thereof. By way of example, a "duplex" includes a cleaved 5' flap sequence (e.g., a primary cleaved flap) hybridized to a complementary cleaved flap-hybridizing sequence of a FRET cassette; and a cassette cleaved flap hybridized to a complementary masking oligonucleotide.

The term "cleaved form," as used herein, refers to a portion of a polynucleotide that has been cleaved from the remainder of the polynucleotide by the action of one or more nucleases. By way of example, a 5' flap sequence is in a "cleaved form" when a primary probe has been cleaved by an endonuclease (e.g., a FEN enzyme), thereby separating the 5' flap portion from the target-hybridizing portion of a flap probe.

The term "single-stranded state," as used herein with reference to a polynucleotide (e.g., an oligonucleotide, a target nucleic acid, etc.), refers to a region of the polynucleotide that is available for base pairing. In the case of a single-stranded polynucleotide having self-complementary regions, the term "single-stranded state" is a reference to a region of the self-complementary polynucleotide that is available for base pairing. By way of example, a cassette cleaved flap is in a single-stranded state prior to hybridizing to a masking oligonucleotide, or after melting that separates the cassette cleaved flap from the masking oligonucleotide.

As used herein, "temperature conditions" used for conducting a reaction refer to the temperature, or range of temperatures, that permit a reaction to take place. Different temperature profiles of different reactions mean that temperature conditions that allow one reaction to take place may not allow a different reaction to take place. The term also applies to temperature profiles that permit hybridization of a masking oligo to a complementary oligo sequence that includes a fluorophore moiety.

As used herein, "optimal" (and grammatical variants thereof) reaction conditions refer to the most favorable reaction conditions for promoting or allowing a reaction to take place. For example, an optimal temperature for performing a secondary reaction would be the temperature at which a FRET cassette was cleaved most efficiently in a reaction mixture (e.g., corresponding to the peak on a plot of fluorescent signal as a function of reaction temperature). Similarly, an optimal temperature range would be a range of most favorable temperature conditions for promoting or allowing a reaction to take place. In certain exemplary embodiments, preferred optimal temperature ranges may include the optimal temperature plus-or-minus 5° C., more preferably plus-or-minus 4° C., more preferably plus-or-minus 3° C., still more preferably plus-or-minus 2° C., and yet still more preferably plus-or-minus 1° C.

As used herein, "attached" (e.g., two things are "attached") means chemically bonded together. For example a fluorophore moiety is "attached" to a FRET cassette when it is chemically bonded to the structure of the FRET cassette.

As used herein, "equivalent" (e.g., in the context of "equivalent donor-acceptor pairs," or "equivalent donor" or "equivalent fluorophore" moieties) means that excitation and emission spectra of detectable chemical species are sufficiently similar or overlapping by wavelength range as to permit detection of fluorescent emission wavelengths in the same channel of an instrument used for monitoring signals.

As used herein, the term "spectral overlap" refers to two or more light spectra with at least one common wavelength.

As used herein, emission from a donor moiety (e.g., a fluorophore) is "quenched" when detectable emission of a photon from the donor is suppressed or prevented because an acceptor moiety (e.g., a quencher) is sufficiently close. For example, emission from a donor moiety is quenched when the donor moiety and the acceptor moiety are both attached to the same FRET cassette. Similarly, emission from a donor or fluorophore moiety attached to a 5' flap cleaved from a FRET cassette can be quenched when the cleaved 5' flap (cassette cleaved flap) hybridizes to a complementary oligo that includes a quencher moiety.

As used herein, "specific" means pertaining to only one (or to only a particularly indicated group), such as having a particular effect on only one (or on only a particularly indicated group), or affecting only one (or only a particularly indicated group) in a particular way. For example, a cleaved 5' flap (e.g., a primary cleaved flap) specific for a FRET cassette will be able to hybridize to that FRET cassette, form an invasive cleavage structure, and promote a cleavage reaction, but will not be able to hybridize to a different FRET cassette (e.g., a FRET cassette having a different cleaved flap-hybridizing sequence) to promote a cleavage reaction. Likewise, a fluorescent 5' flap cleaved from a FRET cassette (a cassette cleaved flap) may hybridize to a masking oligonucleotide specific for that cassette cleaved flap when the sequences of the two oligonucleotides are complementary to each other.

As used herein, the term "specifically hybridizes" means that under given hybridization conditions a probe or primer detectably hybridizes substantially only to the target sequence in a sample comprising the target sequence (i.e., there is little or no detectable hybridization to non-target sequences). Similarly, a cleaved 5' flap that is "specific" for a FRET cassette will be able to specifically hybridize to that FRET cassette to form an invasive cleavage structure and promote a cleavage reaction, but will not hybridize to a different FRET cassette in a manner that forms an invasive cleavage structure.

The term "thermostable" when used in reference to an enzyme, such as a FEN enzyme, indicates that the enzyme is functional or active (i.e., can perform catalysis) at an elevated temperature (e.g., at about 55° C. or higher). In some embodiments, the enzyme is functional or active at an elevated temperature of 65° C. or higher (e.g., 75° C., 85° C., or even 95° C.).

As used herein, the term "amplified" refers to an increase in the abundance of a molecule, moiety or effect. A target nucleic acid may be amplified, for example by in vitro replication such as by PCR.

As used herein, the term "amplification method" as used in reference to nucleic acid amplification means a process of specifically amplifying the abundance of a nucleic acid of interest. Some amplification methods (e.g., polymerase chain reaction, or PCR) comprise iterative cycles of thermal denaturation, oligonucleotide primer annealing to template molecules, and nucleic acid polymerase extension of the annealed primers. Conditions and times necessary for each of these steps are well known in the art. Some amplification methods are conducted at a single temperature and are deemed "isothermal." Accumulation of the products of amplification may be exponential or linear. Some amplification methods (e.g., "target amplification" methods) amplify the abundance of a target sequence by copying it many times (e.g., PCR, NASBA, TMA, strand displacement amplification, ligase chain reaction, LAMP, ICAN, RPA, SPA, HAD, etc.), while some amplification methods amplify the abundance of a nucleic acid species that may or may not contain the target sequence, but the amplification of which indicates the presence of a particular target sequence in the reaction. Some signal amplification methods may increase the abundance of a species of nucleic acid by converting a starting nucleic acid, for example by cleaving the starting nucleic acid to form cleavage products, or by extending it by, for example, polymerization or ligation. A target amplification method may be applied to a signal molecule (e.g., PCR may be used to produce more copies of the product of a ligation, cleavage, or non-target copying reaction), or vice versa.

As used herein, the terms "polymerase chain reaction" and "PCR" refer to an enzymatic reaction in which a segment of DNA is replicated from a target nucleic acid in vitro. The reaction generally involves extension of a primer on each strand of a target nucleic acid with a template dependent DNA polymerase to produce a complementary copy of a portion of that strand. The chain reaction comprises iterative cycles of denaturation of the DNA strands, for example by heating, followed by cooling to allow primer annealing and extension, resulting in an exponential accumulation of copies of the region of the target nucleic acid that is flanked by and that includes the primer binding sites. When an RNA target nucleic acid is amplified by PCR, it is generally converted to a DNA copy strand with an enzyme capable of reverse transcription. Exemplary enzymes include MMLV reverse transcriptase, AMV reverse transcriptase, as well as other enzymes that will be familiar to those having an ordinary level of skill in the art.

The term "oligonucleotide" (sometimes simply "oligo") as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer. Oligonucleotides are typically less than 200 residues long (e.g., between 15 and 100 nucleotides), however, as used herein, the term is also intended to encompass longer polynucleotide chains. The exact size will depend on many factors, which in turn depend on the ultimate function or use of the oligonucleotide. Oligonucleotides are often referred to by their length. For example, a 24 nucleotide oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction). As used herein, the terms "oligonucleotide" and "polynucleotide" may be used interchangeably and may comprise non-naturally occurring monomers, or portions thereof. More particularly, oligonucleotides may include, for example, linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), 2'-O-methyl modifications, phosphorothioate, methylphosphonate, spacers and the like.

As used herein, a "signal" is a detectable quantity or impulse of energy, such as electromagnetic energy (e.g., light). Emission of light from an appropriately stimulated fluorophore is an example of a fluorescent signal. In some embodiments, "signal" refers to the aggregated energy detected in a single channel of a detection instrument (e.g., a fluorometer).

As used herein, a "background" signal is the signal (e.g., a fluorescent signal) generated under conditions that do not permit a target nucleic acid-specific reaction to take place. For example, signal generated in a secondary reaction that includes a FRET cassette and FEN enzyme but not a cassette-specific invasive oligonucleotide (e.g., a primary cleaved flap) would be considered a background signal. In some instances, a background signal is measured in a "negative control" reaction or trial that omits the target nucleic acid.

As used herein a "channel" of an energy sensor device, such as a device equipped with an optical energy sensor, refers to a pre-defined band of wavelengths that can be detected or quantified to the exclusion of other bands of wavelengths. For example, one detection channel of a fluorometer might be capable of detecting light energy emitted by one or more fluorescent labels over a range of wavelengths as a single event. Light emitted as the result of fluorescence can be quantified as relative fluorescence units (RFU) at a given wavelength, or over a band of wavelengths. Examples of common fluorescence detection channels include those that detect fluorescence emission wavelengths in the ranges of from about 510-530 nm (e.g., common for a FAM™ dye detection channel), from about 560-580 nm (e.g., common for a HEX™ dye detection channel), from about 610-650 nm (e.g., common for a TEXAS RED® dye detection channel), from about 675-690 nm (e.g., common for a Cy5® cyanine dye detection channel), and from about 705-730 nm (e.g., common for a QUASAR® 705 dye detection channel). Cy5® dye and ALEXA FLUOR® 647 are examples of two different fluorophores that may be detected in the Cy5® dye channel of a fluorometer.

As used herein, a "threshold" or "threshold cutoff" refers to a quantitative limit used for interpreting experimental results, where results above and below the cutoff lead to different conclusions. For example, a measured signal falling below a cutoff may indicate the absence of a particular target, but a measured signal that exceeds the same cutoff may indicate the presence of that target. By convention, a result that meets a cutoff (i.e., has exactly the cutoff value) is given the same interpretation as a result that exceeds the cutoff.

As used herein, a "threshold cycle number" refers to indicia of amplification that measure the time or cycle number when a real-time run curve signal crosses an arbitrary value or threshold. "TTime" and "Ct" determinations are examples of threshold-based indicia of amplification. Other methods involve performing a derivative analysis of the real-time run curve. For the purpose of this disclosure, TArc and OTArc also can be used to determine when a real-time run curve signal crosses an arbitrary value (e.g., corresponding to a maximum or minimum angle in curvature, respectively). Methods of TTime determination are disclosed in U.S. Pat. No. 8,615,368; methods of Ct determination are disclosed in EP 0640828 B1; derivative-based methods are disclosed in U.S. Pat. No. 6,303,305; and methods of TArc and OTArc determination are disclosed in U.S. Pat. No. 7,739,054. Those having an ordinary level of skill in the art will be aware of variations that also can be used for determining threshold cycle numbers.

As used herein, an "internal calibrator" nucleic acid is a nucleic acid that can be amplified in an in vitro nucleic acid amplification reaction, and that is distinguishable from an analyte nucleic acid (e.g., the target nucleic acid from a test sample) that is coamplified in the same reaction. "Internal" means that the calibrator nucleic acid is amplified and detected within the same reaction mixture as the analyte target nucleic acid, or fragment thereof. In some embodiments, the internal calibrator nucleic acid is amplified by the same primer(s) used for amplifying the analyte nucleic acid that is to be quantified. In other embodiments, different primers are used for this purpose. Generally speaking, the analyte nucleic acid and the internal calibrator nucleic acid differ by at least one nucleotide position that can be discriminated by an invasive cleavage reaction. This allows multiplexed invasive cleavage assays to detect amplified internal calibrator and analyte target nucleic acids independently.

As used herein, a "calibration standard" is a composition that includes a known or predetermined amount of an internal calibrator nucleic acid.

As used herein, a "reaction vessel" or "reaction receptacle" is a container for containing a reaction mixture. Examples include individual wells of a multiwell plate, and plastic tubes (e.g., including individual tubes within a formed linear array of a multi-tube unit, etc.). However, it is to be understood that any suitable container may be used for containing the reaction mixture.

As used herein, "permitting" a reaction to take place means that reagents and conditions are provided by reaction mixture to test for the presence of a particular nucleic acid (e.g., a target DNA, or a cleaved 5' flap), which may or may not be present in the reaction mixture. For example, "permitting" a primary reaction of an invasive cleavage assay to take place means that a reaction mixture includes an invasive probe, a primary probe that includes a 5' flap sequence, and a FEN enzyme under appropriate buffer and temperature conditions to allow cleavage of the primary probe and release of a cleaved 5' flap if a target DNA is also available in the reaction mixture to participate in the primary reaction. Similarly, "permitting" a secondary reaction of an invasive cleavage assay to take place means that a reaction mixture includes a FRET cassette and a FEN enzyme under appropriate buffer and temperature conditions to allow cleavage of the FRET cassette if a cleaved 5' flap specific for the FRET cassette also is available in the reaction mixture to participate in the secondary reaction. Still further, temperature conditions "permitting" (or that "permit" or are "permissive" for) a reaction to take place are temperature conditions that are conducive for conducting or allowing the reaction to proceed.

By "kit" is meant a packaged combination of materials intended for use in conjunction with each other. Kits useful in accordance with the disclosed techniques may include one or more vessels or tubes containing various reagents. Kits further may include instructions, or other information in a "tangible" form (e.g., printed information, electronically recorded on a computer-readable medium, or otherwise recorded on a machine-readable medium such as a bar code).

DETAILED DESCRIPTION

Disclosed herein is a multiplexed nucleic acid amplification and detection system that can be used for detecting the presence of multiple specific nucleic acid sequences in a temperature-dependent fashion using only a single fluorescence detection channel of a nucleic acid analyzer. The technique simplifies multiplex detection of nucleic acid analytes, such as single nucleotide polymorphisms (i.e., "SNPs"), as can be used in diagnostic applications. Conveniently, the technique can be carried out using standard PCR instrumentation equipped for fluorescence detection or monitoring.

The disclosed procedure employs a "masking oligo" that hybridizes by complementary base pairing to a fluorescently labeled 5' flap cleaved from a probe or FRET cassette (e.g., a cassette cleaved flap) in an invasive cleavage assay. The masking oligonucleotide includes a fluorescence quenching moiety (sometimes "quencher" herein) attached thereto. When the hybridization between the masking oligonucleotide and the labeled cleaved flap occurs, the quenching moiety of the masking oligo is brought into proximity of the fluorophore moiety of the cleaved 5' flap. Fluorescent signal emitted by the fluorophore of the cleaved 5' flap is then quenched. When different cleavage products (e.g., cleaved flaps of different length and/or different sequence) are hybridized to cognate masking oligos at appropriate temperatures, it becomes possible to determine identities of secondary reactions that liberated the cassette cleaved flaps, and so determine which target sequences were present in the reaction mixtures.

Invasive Cleavage Reactions and Assays

Unlike other invasive cleavage assays that generate fluorescent signals to indicate the presence of an analyte nucleic acid by cleavage of a FRET cassette, the present technique does not require persistence of the fluorescent signal to determine whether a particular FRET cassette was cleaved. Indeed, the technique described herein actually requires that cleavage of at least one FRET cassette in a multiplex assay produces a fluorescent signal that is quenched or extinguished as a function of temperature of the reaction mixture. This is accomplished by including in the reaction mixture a masking oligonucleotide complementary to a fluorescent cleavage product of the at least one FRET cassette. The hybrid interaction to form a duplex including the fluorescent cleavage product and the complementary masking oligonucleotide is characterized by a melting temperature ($T_m$). At temperatures above the $T_m$, the fluorescent cleavage product is in a single-stranded state where the fluorescent signal can be produced and detected or measured. At temperatures below the $T_m$, duplexes form and quench fluorescence emitted from the fluorophore attached to the 5' flap that cleaved from the 5' flap FRET cassette. By including in the reaction mixture different masking oligos complementary to different fluorescent 5' flap cleavage products, where different duplexes resulting from hybridization of masking oligonucleotides and fluorescent cleavage products exhibit different $T_m$s, it is possible to determine which FRET cassette, among a plurality of FRET cassettes labeled with fluorophores detectable in the same channel of a fluorometer, cleaved to generate the signal. This fluorescence quenching capacity, or temperature-dependent difference in fluorescent signal, is essential to the function of the disclosed technique.

The invasive cleavage assays disclosed herein involve formation of an invasive cleavage structure, and enzymatic cleavage of the invasive cleavage structure by a flap endonuclease (e.g., FEN-1) enzyme. In some embodiments, the invasive cleavage structure includes: (1) a FRET cassette; and (2) an invasive oligonucleotide hybridized to the FRET cassette. In some embodiments, the invasive oligonucleotide hybridized to the FRET cassette is a 5' flap cleaved from a primary probe. In some embodiments, the invasive cleavage assays include: (1) a target nucleic acid that is to be detected; (2) a primary probe having a 5' flap, where a target-complementary sequence of the primary probe is hybridized to the target nucleic acid; and (3) an invasive oligonucleotide hybridized to the target nucleic acid adjacent to and upstream of the hybridized primary probe. In some embodiments, invasive cleavage assays combine first and second invasive cleavage reactions in serial fashion (see FIG. 1), so that a cleaved 5' flap from a primary probe (e.g., sometimes "primary cleaved flap") serves as an invasive oligonucleotide to promote enzymatic cleavage of a FRET cassette in a secondary reaction.

The upstream invasive oligonucleotide of the primary reaction is typically designed to anneal essentially permanently to the target DNA at the assay temperature (e.g., to have a $T_m$ that is substantially above the assay temperature), while the primary probe oligonucleotide is not. The portion of the primary probe that anneals to the target strand is designed to have a $T_m$ with respect to the target strand that is close to the assay temperature, such that the primary probe oligonucleotides in the reaction mixture will constantly anneal and disassociate from the target strand at the reaction temperature without temperature cycling. In some embodiments, the $T_m$ is within about 4° C., more preferably within 3° C., still more preferably within 2° C., and yet still more preferably within 1° C. of the assay temperature. A cleavage structure is formed upon annealing of a primary probe oligonucleotide next to, and downstream of the invasive oligonucleotide. This cleavage structure can be cleaved by a flap endonuclease.

A key feature and principle of operation of invasive cleavage reactions in accordance with the disclosure is that cleavage products can increase in number and accumulate under isothermal conditions (i.e., without temperature cycling). For example, primary probe oligonucleotides that hybridize to target nucleic acid can repeatedly anneal and dissociate without temperature cycling. A single site on a target DNA can be reused or recycled, to hybridize to a succession of new uncleaved probes without temperature cycling, generating thousands of cleaved probes for each target molecule. See, e.g., Olivier, *Mutat Res*, 573: 103-110 (2005). Likewise, fluorescent signal resulting from FEN-1 cleavage of FRET cassettes, following cycling hybridization to a 5' flap cleaved from a primary probe, also increases and accumulates under isothermal conditions.

Invasive cleavage assays can also be configured to operate in a sequential fashion, in which a cleaved flap from a primary invasive cleavage reaction is used to form a second cleavage structure. For example, the SISAR assay of Hall uses two sequential signal amplification reactions to multiply the total amount of signal generated by an assay (See Hall et al., *Proc. Natl. Acad. Sci.*, U.S.A. 97 (2000) 8272-8277). In the SISAR assay illustrated in FIG. 1, cleavage of each primary probe releases a cleaved 5' flap ("Primary cleaved flap" in FIG. 1). The cleaved flap hybridizes to a hairpin "FRET cassette" oligonucleotide to form a second cleavage structure. Cleavage of the second cleavage structure separates the fluorophore dye from the quenching moiety of the FRET cassette, thereby making fluorescence from the fluorophore detectable.

Invasive cleavage assays employing a FRET cassette (e.g., serial invasive cleavage assays) typically are designed so that the cleaved flap-FRET cassette complex has a $T_m$ close to the assay temperature (e.g., within 4° C., more preferably within 3° C., still more preferably within 2° C., and yet still more preferably within 1° C. of the assay temperature), so that cleaved flaps will constantly anneal and disassociate from the FRET cassette at the reaction temperature, and without temperature cycling. Upon annealing of a cleaved flap to a FRET cassette, a cleavage structure is formed, and the structure can be cleaved by a flap endonuclease (e.g., FEN-1 endonuclease). Thus, the secondary reaction that involves cleavage of a FRET cassette generates a signal using the same recycling principle as the primary reaction. Each cleaved flap can hybridize to a succession of new uncleaved FRET cassettes without temperature cycling, thereby generating thousands of unquenched fluorophores for each cleaved flap.

A flap endonuclease (e.g., FEN-1) enzyme present in a reaction mixture that further includes the analyte nucleic acid, the invasive probe, the primary probe, and a FRET cassette will cleave the 5' flap from the remainder of the primary probe when there is a single-base overlap between the invasive probe and the primary probe when both are hybridized to the analyte nucleic acid. This cleavage reaction is termed the "primary" reaction. The 5' flap released from the primary probe then undergoes cycling hybridization to the FRET cassette, which has a sequence complementary thereto, whereupon a FEN-mediated cleavage reaction separates a fluorophore from a quencher moiety present on the same FRET cassette to result in a detectable fluorescent emission. This cleavage reaction that generates a fluorescent signal by cleavage of the FRET cassette is termed the "secondary" reaction. As described above, if the secondary reaction is carried out at a temperature close to the $T_m$ (i.e., melting temperature) of the duplex between the 5' flap cleaved from the primary probe and the FRET cassette to facilitate cycling hybridization, then the same 5' flap is free to interact with similar cognate FRET cassettes to further catalyze cleavage reactions. This linear amplification, which can occur at a fixed temperature, is detectable by increased fluorescence as a function of time. Each of the primary and secondary reactions is essentially an isothermal process. Indeed, the FEN-1 dependent secondary invasive cleavage reaction generates detectable fluorescent signal without the requirement for polymerization, even under thermal conditions where thermostable DNA polymerases (e.g., Taq DNA polymerase) exhibit severely compromised polymerization activity. Indeed, polymerase-based extension of a cleaved 5' flap using the FRET cassette as a template would compromise the cycling hybridization which benefits fluorescent signal accumulation. Accordingly, extension of the cleaved 5' flap is contraindicated.

Useful Fluorophores and Quenchers

In some embodiments, multiplexed invasive cleavage assays in accordance with the presently disclosed technique may employ only a single detection channel for detecting fluorescent signals generated by multiplexed invasive cleavage assays, and preferably will use the same chemical species of fluorophore for signal generation from different targets in the multiplexed reaction. In other embodiments, multiple different fluorophores may be combined for signal generation from different targets in the multiplexed reaction. Exemplary fluorophores that find use in the FRET cassette systems of the presently disclosed technique include, but are not limited to: fluorescein, rhodamine, REDMOND RED® dye, YAKIMA YELLOW® dye, 2',4',5',7',1,4-hexachlorofluorescein (HEX™ dye), N,N,N',N'-tetramethyl-6-carboxyrhodamine (TAMRA) dye, ROX™ dye, Cy3@cyanine dye, Cy3.5@cyanine dye, Cy5® cyanine dye, Cy5.5® cyanine dye, and Cy7® cyanine dye, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, TEXAS RED® dye, eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid, 6-carboxyfluorescein (6-FAM™ dye), 2',4',1,4,-tetrachlorofluorescein (TET dye), 2',7'-dimethoxy-4',5'-dichloro-6-carboxyrhodamine (JOE dye), 2'-chloro-5'-fluoro-7',8'-fused phenyl-1,4-dichloro-6-carboxyfluorescein (NED dye), 2'-chloro-7'-phenyl-1,4-dichloro-6-carboxyfluorescein (VIC dye), fluorescein isothiocyanate (FITC), 5,6-carboxymethyl fluorescein, nitrobenz-2-oxa-1,3-diazol-4-yl (NBD), coumarin, dansyl chloride, amino-methyl coumarin (AMCA), Erythrosin, BODIPY® dye, CASCADE BLUE® dye, OREGON GREEN® dye, pyrene, lissamine, xanthenes, acridines, oxazines, phycoerythrin, QUANTUMDYE™ dye, thiazole orange-ethidium heterodimer, and the like.

Exemplary quenchers for use in the FRET cassette systems of the technology include, but are not limited to: cyanine dyes, such as Cy3® cyanine dye, Cy3.5® cyanine dye, Cy5® cyanine dye, Cy5.5® cyanine dye, and Cy7® cyanine dye, rhodamine dyes, such as tetramethyl-6-carboxyrhodamine (TAMRA dye) and tetrapropano-6-carboxyrhodamine (ROX™ dye), DABSYL dye, DABCYL dye, nitrothiazole blue (NTB), anthraquinone, malachite green, nitrothiazole, or nitroimidazole compounds, QSY™7 quencher moiety (Molecular Probes, Eugene, OR), ECLIPSE® quencher (Epoch Biosciences, Inc., Logan UT), and the like. Alternative quenchers include Black Hole Quencher dyes, particularly BHQ™-1 dye, BHQ™-2 dye, and BHQ™-3 dye (Biosearch Technologies, Petaluma CA); BLACKBERRY® quencher moieties (Berry & Associates, East Dexter, MI); and IOWA BLACK® quencher moiety (Integrated DNA Technologies, Coralville, IA). Analysis of factors such as absorbance and emission spectra of various molecules in selection of pairs or groups of moieties for use in FRET configurations is well known to those of skill in the art.

Those having an ordinary level of skill in the art will be aware of wavelength ranges that can be detected by different channels of a fluorometer, and so easily will be able to select fluorophores for different FRET cassettes, where emissions from the different fluorophores can be detected in the same fluorometer channel.

Features of the Temperature-Dependent Multiplexing Technique

Unlike prior invasive cleavage assays that benefit from uninterrupted persistence of fluorescent signals, the presently disclosed technique benefits from selective suppression of fluorescence following FEN-1 mediated cleavage of a FRET cassette. Peterson et al., in published U.S. Pat. App. 2018/0163259 A1 disclosed a method wherein different FRET cassettes labeled with the same fluorophores were cleaved at different temperatures, where the different temperatures essentially isolated one reaction from the other. Monitoring the accumulated fluorescent signal as a function of time or cycle number allowed resolution of activity of the FRET cassettes. In this way, a plurality nucleic acid targets could be detected in a multiplex format using only a single channel of a fluorometer, and even using only a single type of fluorescent label. As disclosed herein, the present technique relies on temperature-dependent fluorescence quenching to effectively remove the contributions of fluorescent signals arising from different FRET cassettes, even if the different FRET cassettes harbor identical fluorescent labels. Thus, procedures or events taking place following the FRET cassette cleavage are informative in the presently disclosed technique.

Figure 2:
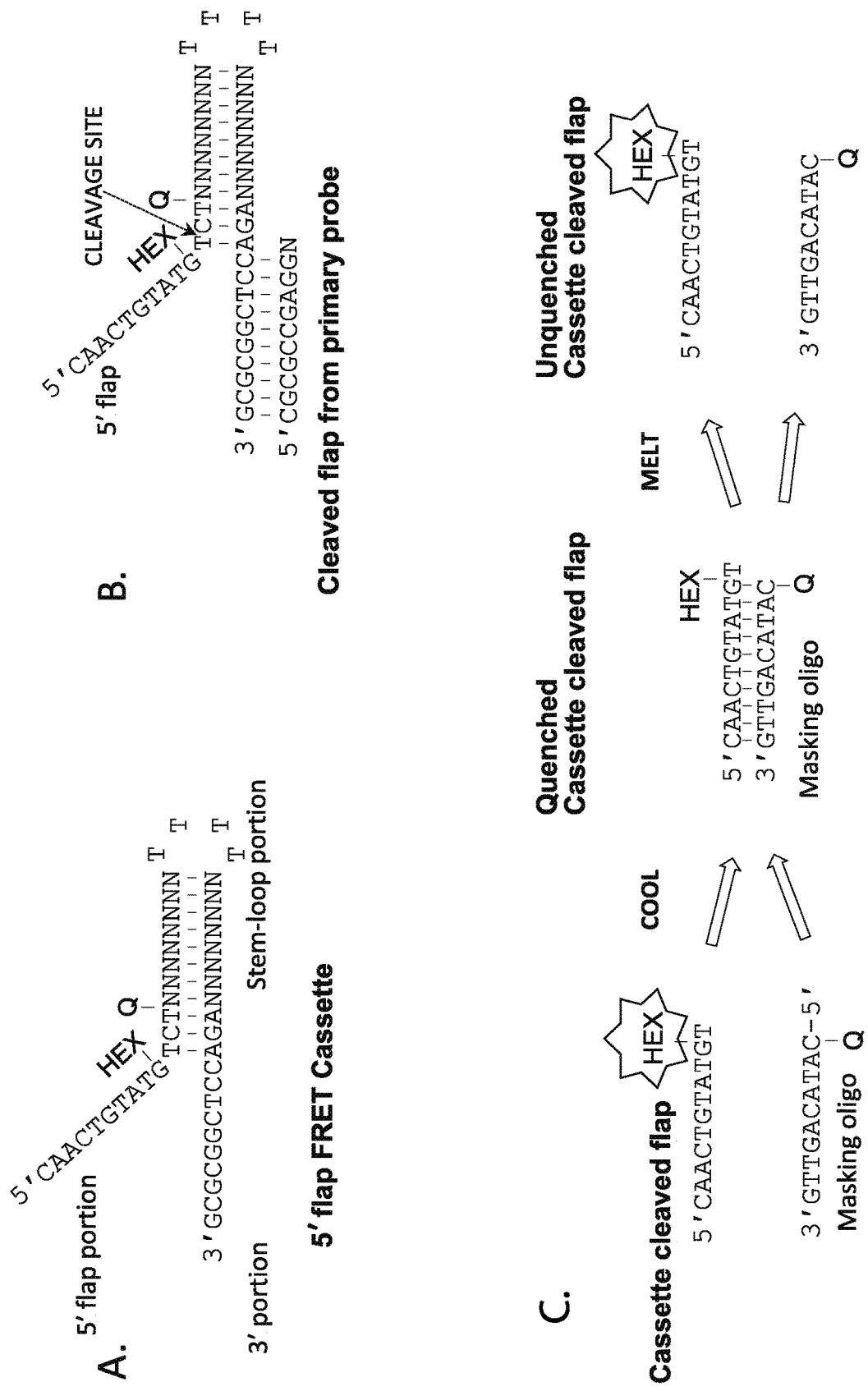
FIG. 2 presents a series of schematic diagrams illustrating the structure and use of 5' flap FRET cassettes.

The present technique employs at least one FRET cassette structured to include a 5' flap portion that retains the fluorophore following cleavage by a FEN-1 enzyme in a secondary reaction. Preferably, lengths of the 5' flaps fall in the range of from 8 to 30 nucleotides, more preferably from 8 to 25 nucleotides, yet still more preferably from 8 to 16 nucleotides. Particularly preferred 5' flap lengths are 9 nucleotides, 10 nucleotides, 11 nucleotides, 12 nucleotides, 13 nucleotides, 14 nucleotides, or 15 nucleotides. FIG. 1 illustrates a serial invasive cleavage reaction, where the FRET cassette is a flapless FRET cassette that does not include a 5' flap portion, and where cleavage in the secondary reaction liberates a fluorescent dye attached to a single nucleotide. In contrast, a 5' flap FRET cassette (see FIG. 2A) can hybridize by cycling hybridization to a cleaved flap from a primary probe (see FIG. 2B) to produce a structure cleavable by a FEN-1 enzyme. The resulting cassette cleaved flap emits a fluorescent signal when in a single-stranded state, but that signal can be reversibly suppressed or quenched by hybridization of the cassette cleaved flap to a masking oligo that includes a quenching moiety (see FIG. 2C). The hybrid interaction between the cassette cleaved flap and the masking oligo can be controlled in a temperature-dependent fashion. When used in the same reaction mixture, the flapless FRET cassette and the 5' flap FRET cassette can produce signals resolvable by temperature changes after the cleavage reactions have occurred.

Figure 3:
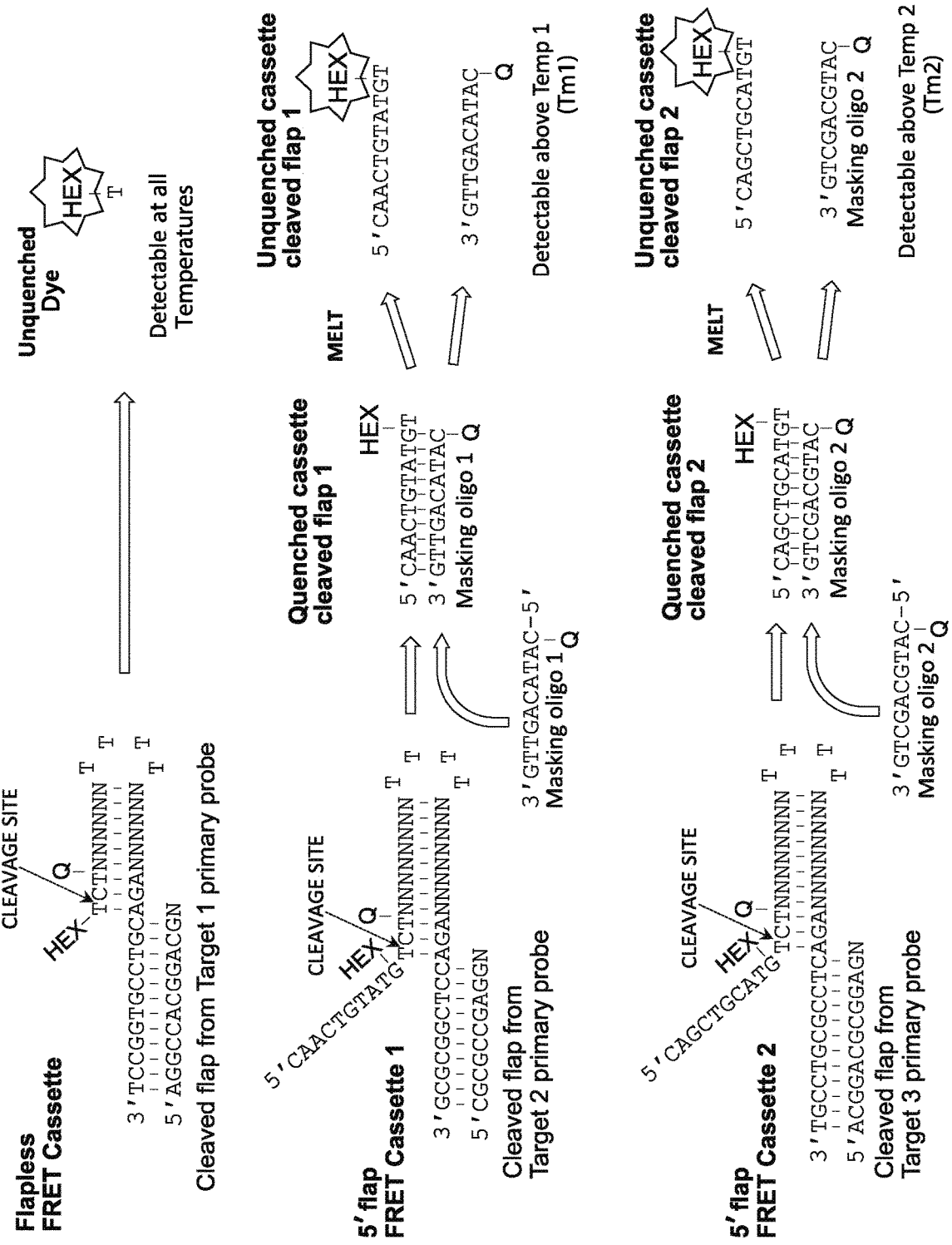
FIG. 3 schematically illustrates how fluorescent signals produced by cleavage of three different FRET cassettes ("flapless FRET cassette" (SEQ ID NO:11); "5' flap FRET cassette 1" (SEQ ID NO:7); and "5' flap FRET cassette 2" (SEQ ID NO:13)) can be distinguished by temperature-dependent quenching. "Cleaved flap from Target 2 primary probe" (SEQ ID NO:8) hybridizes to "5' flap FRET cassette 1" (SEQ ID NO:7) to promote an enzyme-dependent cleavage reaction. "Cassette cleaved flap 1" (SEQ ID NO:9), or the 5' flap cleaved from "5' flap FRET cassette 1" (SEQ ID NO:7), can hybridize to "masking oligo 1" (SEQ ID NO:10) to form a first hybrid duplex exhibiting quenched fluorescence. "Cleaved flap from Target 3 primary probe" (SEQ ID NO:14) hybridizes to "5' flap FRET cassette 2" (SEQ ID NO:13) to promote an enzyme-dependent cleavage reaction. "Cassette cleaved flap 2" (SEQ ID NO:15), or the 5' flap cleaved from "5' flap FRET cassette 2" (SEQ ID NO:13), can hybridize to "masking oligo 2" (SEQ ID NO:16) to form a second duplex exhibiting quenched fluorescence. The two hybrid duplexes are designed to have unique melting/annealing properties, which allows for distinguishing one from the other. The signal produced by cleavage of the "flapless FRET cassette" (SEQ ID NO:11) remains detectable under all temperature conditions.

In addition to distinguishing the origin of fluorescence arising from a flapless FRET cassette (no 5' flap portion) and a 5' flap FRET cassette, the disclosed technique permits resolution of signals arising from identical fluorescent dyes of different 5' flap FRET cassettes. FIG. 3 schematically illustrates how fluorescent signals produced by three different FRET cassettes (Flapless FRET cassette; 5' flap FRET cassette 1; and 5' flap FRET cassette 2), each FRET cassette being labeled with a fluorophore detectable in the same channel of a fluorometer (e.g., identical fluorophores), can be distinguished from each other under different temperature conditions. The upper portion of the diagram shows a flapless FRET cassette that does not include a 5' flap. This FRET cassette, following cycling hybridization to a complementary cleaved flap from a primary probe, can be cleaved by a FEN-1 endonuclease to release a fluorescent dye, where fluorescence emitted from the released dye cannot be quenched by interaction with any masking oligonucleotide used in the reaction. Fluorescence emitted from this unquenched dye is detectable at all temperatures. The middle portion of the diagram in FIG. 3 shows a first 5' flap FRET cassette (5' flap FRET cassette 1) that can be cleaved by a FEN-1 enzyme to release a 5' flap ("Cassette cleaved flap 1") following cycling hybridization to a complementary cleaved 5' flap from a primary probe. Cassette cleaved flap 1 remains attached to the fluorophore following the cleavage reaction, but fluorescent signal is quenched if Cassette cleaved flap 1 hybridizes to a complementary Masking oligo. This can occur at a temperature below the $T_m$ for the hybrid duplex that includes the Cassette flap 1 and the complementary Masking oligo. A fluorescent signal can be emitted by the fluorophore of Cassette cleaved flap 1 if the temperature is raised above this $T_m$ ("$T_m1$") so that Cassette cleaved flap 1 is in a single-stranded state ("Unquenched cassette cleaved flap 1" in the diagram). The lower portion of the diagram in FIG. 3 shows a second 5' flap FRET cassette (5' flap FRET cassette 2) that can be cleaved by a FEN-1 enzyme to release a 5' flap ("Cassette cleaved flap 2") following cycling hybridization to a complementary cleaved 5' flap from a primary probe. Cassette cleaved flap 2 remains attached to the fluorophore following the cleavage reaction, but fluorescent signal is quenched if Cassette cleaved flap 2 hybridizes to a complementary Masking oligo. This can occur at a temperature below the $T_m$ for the hybrid duplex that includes the Cassette cleaved flap 2 and the complementary Masking oligo). A fluorescent signal can be emitted by the fluorophore of Cassette cleaved flap 2 if the temperature is raised above this $T_m$ ("$T_m2$") so that Cassette cleaved flap 2 is in a single-stranded state ("Unquenched cassette cleaved flap 2" in the diagram). Designing the different 5' flap FRET cassettes to harbor 5' flap portions with different $T_m$s (e.g., by having different lengths and/or G:C contents) permits the signals arising from the different cleaved flaps to be distinguished from each other. For example, signals emitted by fluorophores of the different cassette cleaved flaps can be monitored: (1) such that the fluorophore of only one of the cassette cleaved flaps emits a signal at one time; or (2) as a function of temperature to determine a melting profile. Both of these alternatives are illustrated in the working Examples, herein.

Notably, in procedures employing a plurality of different 5' flap FRET cassettes and masking oligos, the $T_m$s for hybrid duplexes including 5' flap cleavage products ("cassette cleaved flaps") and cognate masking oligos preferably must be different. Preferably, the $T_m$s of the different hybrid duplexes being analyzed in the same multiplex reaction (e.g., whether a real time nucleic acid amplification reaction, or an endpoint melting/annealing analytical procedure) differ by at least 2° C., more preferably by at least 3° C., more preferably by at least 5° C., more preferably by at least 7° C., more preferably by at least 10° C., or even by at least 15° C. Preferred differences between $T_m$s for hybrid duplexes including cassette cleaved flaps and cognate masking oligos range from 2° C. to 20° C. different, more preferably from 5° C. to 20° C. different, more preferably from 5° C. to 15° C. different, or even more preferably from 5° C. to 10° C. different. In some embodiments, a masking oligonucleotide and/or the 5' flap of the FRET cassette oligonucleotide may comprise one or more nucleotide modifications to adjust or alter the $T_m$ of the masking oligonucleotide-cassette cleaved flap duplex. For example, in some embodiments, the one or more nucleotide modifications is selected from the group consisting of Locked Nucleic Acid (LNA), Peptide Nucleic Acid (PNA), Bridged Nucleic Acid (BNA), 2'-0 alkyl substitution, L-enantiomeric nucleotide, or combinations thereof.

Figure 4:
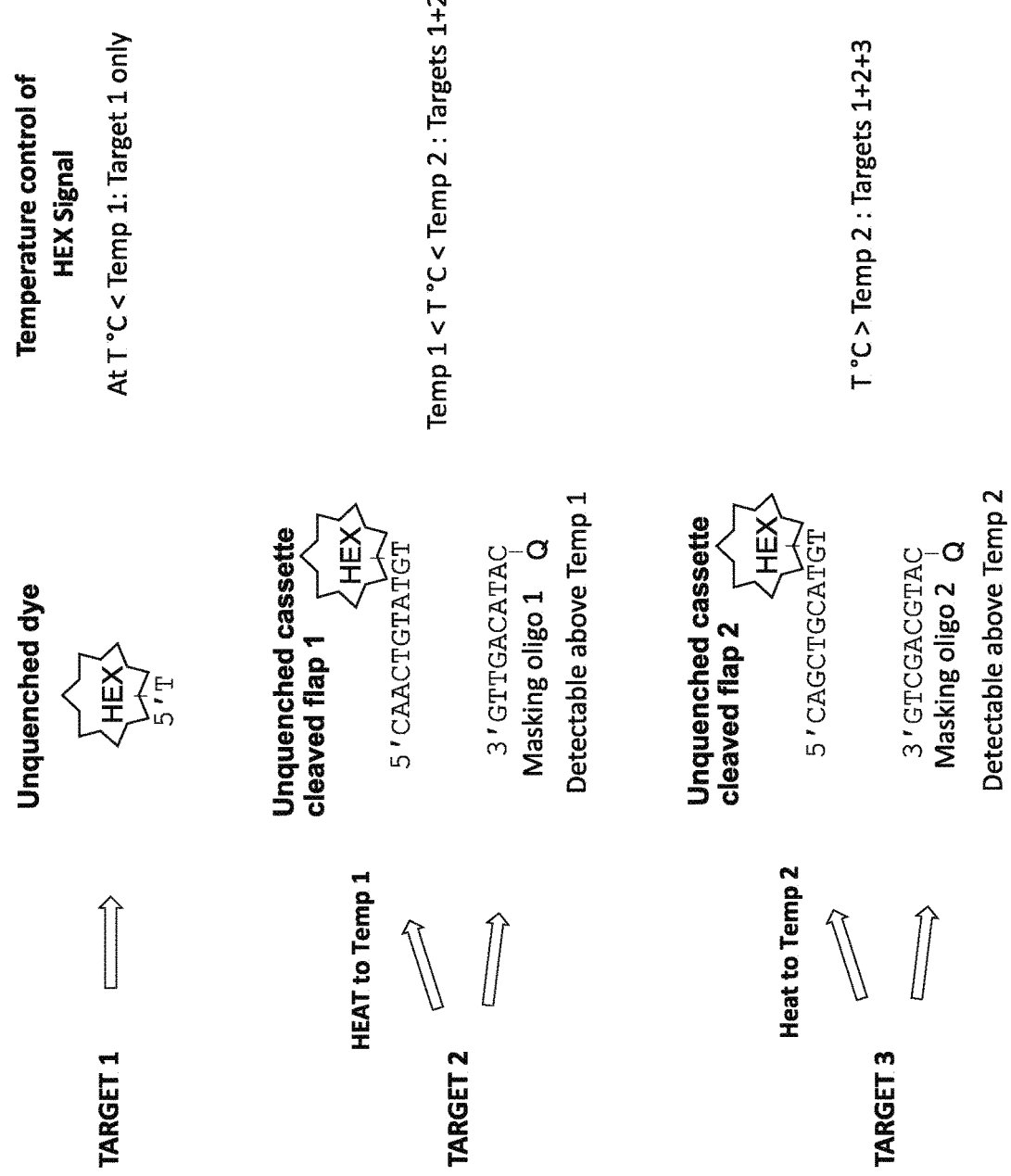
FIG. 4 is a schematic diagram of cleavage products prepared using a flapless FRET cassette and two different 5' flap FRET cassettes, where all three FRET cassettes are labeled with the same reporter dye (HEX™ dye). The different FRET cassettes permit detection of different nucleic acid target sequences using only a single fluorescence detection channel of a nucleic acid analyzer. In the illustrated embodiment, Temp 1 is lower than Temp 2 (e.g., Temp 1 may be 40° C. and Temp 2 may be 50° C.). Detection of Target 1 is done using a flapless FRET cassette (e.g., SEQ ID NO:11 from FIG. 3) that does not have a corresponding masking oligonucleotide, such that the signal from Target 1 is detectable at all temperatures. Detection of Target 2 is done with a 5' flap FRET cassette (e.g., SEQ ID NO:7 from FIG. 3) that produces "cassette cleaved flap 1" (SEQ ID NO:9), which is masked by hybridization with "masking oligo 1" (SEQ ID NO:10) when the reaction mixture is below Temp 1. Above Temp 1 but below Temp 2, signals reflecting detection of both Target 1 and Target 2 are detectable. Detection of Target 3 is done with a 5' flap FRET cassette (e.g., SEQ ID NO:13 from FIG. 3) that produces "cassette cleaved flap 2" (SEQ ID NO:15), which is masked by hybridization with "masking oligo 2" (SEQ ID NO:16) when the reaction mixture is below Temp 2. Above Temp 2, signal from all three of Targets 1, 2, and 3 is detectable. In the embodiment illustrated, the temperature selected for detection of cleavage of the different FRET cassettes is independent of the sequences of the three different target nucleic acids.

FIG. 4 schematically illustrates identification of different target sequences by detecting FEN-1 mediated cleavage products of different FRET cassettes, where each FRET cassette harbors a fluorescent dye that can be detected in the same channel of a fluorometer (e.g., shown as identical HEX™ fluorophores). Indicated cleavage products and Masking oligos correspond to those presented in FIG. 3. Fluorophore-containing cleavage products from a Flapless FRET cassette (upper), indicating the presence of Target 1, remain unquenched at all temperatures. Thus, at a temperature below Temp 1, where cassette cleaved flap 1 and cassette cleaved flap 2 are hybridized to their respective Masking oligos, detectable fluorescence indicates the presence of Target 1. Fluorophore-containing cleavage products from 5' flap FRET cassette 1, indicating the presence of Target 2 (middle), are unquenched at a temperature above Temp 1. At a temperature above Temp 1 and below Temp 2, detectable fluorescence can indicate the presence of Target 1 and Target 2. Since the fluorescent signal measured in the procedure is additive, the difference between fluorescent signal measured above Temp 1 but below Temp 2 (middle portion of FIG. 4) and fluorescent signal measured below Temp 1 (upper portion of FIG. 4) indicates signal due to the presence of Target 2. Fluorophore-containing cleavage products from 5' flap FRET cassette 2, indicating the presence of Target 3 (lower), are unquenched at temperatures above Temp 2. At a temperature above Temp 2, detectable fluorescence can indicate the presence of Target 1 and Target 2 and Target 3. Thus, the difference between fluorescent signal measured above Temp 2 (lower portion of FIG. 4) and fluorescent signal measured above Temp 1 but below Temp 2 (middle portion of FIG. 4) indicates signal due to the presence of Target 3. In this illustration, Temp 1

2<Temp 3. Comparing results of fluorescence detection at the different temperatures can be used to determine which Target was responsible for promoting the cleavage reaction(s). In some embodiments, this involves comparing magnitudes of fluorescent signals, where signals measured at different temperatures are the additive results of the known detectable fluorescence, as described immediately above. In some embodiments, determining which Target was responsible for promoting cleavage reaction(s) involves performing a melting/annealing curve analysis.

Results Processing and Apparatus

Procedures disclosed herein can be carried out using a conventional laboratory apparatus that amplifies nucleic acid and monitors amplicon production, including an apparatus having an integrated or standalone computer or processor programmed with appropriate software. Included within the meaning of "computer" is an embedded processor controlled by software. The computer can be programmed, either by a manufacturer or an end user, to execute one or more temperature changes or steps, preferably allowing for monitoring of fluorescence within a reaction mixture as cycles of the amplification reaction are occurring. Preferably, reaction mixtures are contained within a reaction vessel (e.g., a tube, or well of a multiwell plate) held within the nucleic acid-amplifying apparatus. However, it is also possible for analysis of amplification products to be completed after the amplification reaction is complete (e.g., to establish a melting/annealing curve for amplification products). This latter analysis can even be completed outside the apparatus that amplified nucleic acids.

A computer component of an apparatus useful for performing the disclosed technique can be programmed with software instructions that "cause" the computer to perform certain steps. These steps may involve any of: controlling of a thermocycler that amplifies nucleic acids; receiving inputs from a fluorometer that monitors fluorescence emission in a reaction mixture where FRET cassette cleavage takes place in an invasive cleavage reaction; or processing results to determine which of two or more FRET cassettes cleaved to generate a fluorescent signal. In preferred embodiments, FRET cassettes cleave to generate fluorescent cleavage products, where fluorescence produced by the different cleavage products can be detected or measured in a single channel of the fluorometer. In some embodiments, the different FRET cassettes are labeled with identical fluorophores. A computer also can be used to perform mathematical steps (e.g., addition, subtraction, multiplication, and/or division) leading to a determination about which FRET cassette in a mixture cleaved to result in a detectable or measurable fluorescent signal.

Methods disclosed herein can be carried out using an automated nucleic acid analyzer, such as a device that amplifies nucleic acids and monitors production of nucleic acid amplification products. These analyzers include PCR instruments, or real-time PCR instruments that can be programmed to execute a series of temperature cycling steps. Preferably, the PCR instrument is equipped with a fluorometer that monitors progress of reactions taking place within tubes or wells of a multiwell plate (generally, reaction "receptacles"). Instruments configured for performing and monitoring real-time PCR reactions are particularly preferred for use with the disclosed techniques. One example of a preferred apparatus for performing, monitoring, and assessing results obtainable with the disclosed techniques is the Panther Fusion System (Hologic, Inc.; San Diego, CA), which advantageously automates steps of the procedure. Another preferred apparatus is the ABI 7500 Real-Time PCR System (ThermoFisher Scientific; NY).

One general approach for assessing the status of fluorescent cleavage products among a mixture of a flapless FRET cassette and one or more 5' flap FRET cassettes involves separately assessing cleavage of the two types of FRET cassette. This procedure may involve reducing the reaction mixture temperature below the lowest $T_m$ for any duplex formed between a masking oligonucleotide and a fluorescent cleavage product of a 5' flap FRET cassette in the mixture. The result is that residual fluorescent signal originates from a fluorescent cleavage product that cannot be quenched, and so would exhibit a constant value on a first derivative plot of change in fluorescence as a function of temperature. Thus, measuring or detecting residual fluorescent signal (e.g., specific signal that exceeds background fluorescence) when fluorescence from other fluorescent cleavage products is quenched as the result of duplex formation with masking oligonucleotides can indicate the presence of a non-quenchable fluorescent cleavage product. Detecting fluorescent signal under this condition can indicate the non-quenchable fluorescent cleavage product is present in the reaction mixture, and so that the corresponding FRET cassette was cleaved. In a second step, a temperature-dependent melting/annealing curve (sometimes "quenching profile") can be prepared for the reaction mixture containing fluorescent cleavage products, and a derivative plot prepared therefrom. For example, a first derivative plot of fluorescence change as a function of temperature will include peaks or maxima corresponding to different duplexes present in the reaction mixture, where duplex formation quenches signal from fluorescent cleavage products contained therein. In this way, it is possible to determine which FRET cassette(s) cleaved to produce fluorescent cleavage products.

Example systems are illustrated herein by multiplex detection of either two or three analytes using invasive cleavage of different FRET cassettes, where the FRET cassettes harbor fluorescent labels that can be detected or monitored in a single channel of a fluorometer or a fluorescence-monitoring apparatus. In some embodiments, multiple FRET cassettes were used in the multiplex procedure. For example, two different FRET cassettes can be combined in a single reaction mixture, where only one of the FRET cassettes harbors a 5' flap sequence complementary to a masking oligonucleotide included in the same reaction mixture. The other FRET cassette can be a flapless FRET cassette that does not include any 5' flap sequence, or alternatively can be a 5' flap FRET cassette in a reaction mixture that does not include a complementary masking oligonucleotide. In such cases, fluorescent signal resulting from cleavage of only one of the two FRET cassettes would be subject to temperature-dependent fluorescence quenching. As indicated above, fluorescent signal generated by cleavage of the FRET cassette, where the fluorescent cleavage product does not interact with any masking oligonucleotide to quench fluorescence, maintains substantially constant as temperature of the reaction mixture changes. Detection of this non-quenchable fluorescent cleavage product can involve detecting fluorescent signal (e.g., fluorescent signal above background) at a temperature where formation of duplexes comprising masking oligonucleotides quenches fluorescent signals from all other quenchable fluorescent cleavage products monitored in the same fluorescence channel in the reaction mixture. Detection of a quenchable fluorescent cleavage product in the multiplex reaction mixture can involve simply establishing that measurable fluorescent signal is greater at a temperature above the $T_m$ for masking oligo duplex formation compared to a temperature below the $T_m$ where fluorescent quenching is maximal.

In a different embodiment, the multiplex reaction mixture includes two different FRET cassettes, where each of the FRET cassettes includes a cleavable 5' flap sequence, and where fluorescent signal emitted by each cleaved 5' flap can be quenched by hybridization to a different complementary masking oligonucleotide. Determining which FRET cassette cleaved in the reaction mixture can involve a derivative analysis, preferably involving a first derivative plot of a melting/annealing curve, also as indicated above. By this approach, a plurality of cleavage products can be resolved and identified in a single procedure.

In some embodiments, the multiplex invasive cleavage reaction includes three or more different FRET cassettes, each being labeled with a fluorescent label detectable in a single channel of a fluorometer (e.g., all fluorescent labels can be the same). The FRET cassettes can each harbor a different cleavable 5' flap sequence that emits a fluorescent signal following cleavage, where the fluorescent signal can be quenched in a temperature-dependent fashion following hybridization of a complementary masking oligonucleotide. When duplexes formed by hybridization of the different fluorescent cassette cleaved flaps are characterized by different $T_m$s, identities of the duplexes can easily be determined by assessing the melting/annealing characteristics (e.g., using derivative analysis). This is illustrated below using a first derivative plot to detect and identify duplexes including a fluorescent cleavage product hybridized to a masking oligonucleotide. Still further, one of the FRET cassettes used in the multiplex reaction can produce a fluorescent cleavage product that does not quench in the reaction mixture. In this situation, the aggregated cleavage products can still be said to exhibit different temperature-dependent fluorescence quenching profiles, because some will exhibit fluorescence quenching at different temperatures while one exhibits no fluorescence quenching. Practically speaking, the different cleavage products can be distinguished by monitoring fluorescent signals as the temperature of the reaction mixture is changed. This may involve monitoring fluorescent signals as the temperature is changed from high to low (e.g., to permit annealing of complementary strands to form duplexes), or alternatively changed from low to high (e.g., to promote melting of preformed duplexes). For this reason, temperature-dependent fluorescence quenching profiles are sometimes referred to as "melting/annealing" curves or profiles.

Results from differential quenching of fluorescent cleavage products produced in multiplex invasive cleavage reactions can be analyzed by different approaches to determine which of alternative FRET cassettes cleaved to produce a fluorescent signal detectable in a single channel of a fluorometer or fluorescent detection device. Two preferred analytical approaches that can be automated (e.g., by a computer, a processor, or a controller) involve: (1) evaluating differences between fluorescent readings or measurements at temperatures where different fluorescent cleavage products are subject to greater or lesser fluorescence quenching due to masking oligonucleotide hybridization; and (2) evaluating fluorescence quenching profiles (i.e., fluorescence measured as a function of temperature in the presence of complementary masking oligonucleotides), for example using a mathematical derivative analysis to identify duplexes formed in a reaction mixture by their characteristic melting temperatures (i.e., "$T_m$s"). In certain preferred embodiments, a combination of these different approaches can be used to resolve which of a plurality of different FRET cassettes cleaved in a reaction mixture, where different cleavage products harbor fluorophores that are detected in the same channel of a fluorometer. In some embodiments, the different FRET cassettes harbor identical fluorophores. For example, a reaction mixture containing a fluorescent cleavage product that does not interact with a masking oligonucleotide to effect quenching, together with one or more fluorescent cleavage products that hybridize cognate masking oligonucleotides preferably are analyzed by evaluating differences between fluorescence measured above and below the $T_m$ of a duplex comprising a masking oligonucleotide and a complementary fluorescent cleavage product of a 5' flap FRET cassette, as well as a derivative plot (e.g., a first derivative plot) of change in fluorescence as a function of temperature.

Cleavage of FRET cassettes in a multiplex invasive cleavage assay to generate two fluorescent cleavage products, where only one is subject to temperature-dependent quenching, can be analyzed by assessing fluorescent emissions at two temperatures, or alternatively using this assessment approach together with curve analysis to identify duplexes by $T_m$. A fluorescent cleavage product that cannot be quenched in the reaction mixture remains uniformly fluorescent across the measured temperature range, and so has a constant slope (i.e., zero slope) on a plot of fluorescence as a function of temperature. A first derivative plot of changing fluorescence as a function of temperature will not exhibit any maxima indicative of a $T_m$ for any duplex. In contrast, a first derivative plot indicating the presence of a fluorescent cleavage product subject to temperature-dependent quenching (i.e., due to masking oligonucleotide hybridization) will exhibit a peak indicating the $T_m$ of the duplex that includes the fluorescent cleaved 5' flap. Still further, simple assessment of measured fluorescent signals at two temperatures can indicate the presence or absence of each of two fluorescent cleavage products. More particularly, fluorescence can be measured or detected at one temperature above the $T_m$ of the duplex in the reaction mixture (i.e., a temperature where there is no fluorescence quenching), and at a second temperature below the $T_m$ of the duplex in the reaction mixture (i.e., a temperature where there duplexes are formed; complete fluorescence quenching).

In some instances, a single non-quenchable fluorescent cleavage product (e.g., arising from cleavage of a flapless FRET cassette, or a cassette cleaved flap in the absence of a complementary masking oligonucleotide) is present in a reaction mixture with one or more quenchable fluorescent cleavage products. The fluorescent cleavage product that is not subject to quenching by masking oligonucleotide hybridization is determined to be present if detectable fluorescent signal in a fluorometer channel is measured at the temperature below the $T_m$ of the duplex containing the other fluorescent cleavage product where fluorescence quenching in the fluorometer channel is maximal. Stated differently, measurable fluorescence (i.e., specific signal above a threshold of background signal) at a point where duplexes quench fluorescence from other cleavage products in the reaction mixture indicates the presence of fluorescent cleavage products that are not subject to quenching by masking oligonucleotide hybridization. The fluorescent cleavage product that is subject to quenching by masking oligonucleotide hybridization can be determined to be present if the measured fluorescent signal at the temperature above the $T_m$ (e.g., a temperature where fluorescence quenching is minimal) exceeds the fluorescent signal measured at the temperature below the $T_m$ (i.e., a temperature where fluorescence quenching is complete).

In some embodiments, particularly where multiple different fluorescent cleavage products subject to quenching by masking oligonucleotide hybridization are combined with one fluorescent cleavage product that is not subject to quenching, it is desirable to use both approaches in combination. In such instances melting/annealing curves can be generated and assessed by derivative analysis to determine the presence of quenchable fluorescent cleavage products by detecting $T_m$s of duplexes that quench fluorescence. As well, points on the melting/annealing curves corresponding to complete fluorescence quenching and/or the absence of fluorescence quenching can be used in the above-indicated assessment. More particularly, the presence of a fluorescent cleavage product that is not subject to quenching can be assessed at a reduced temperature where quenching due to masking oligonucleotide hybridization is complete. Detecting a residual fluorescent signal when quenching is complete (i.e., maximal) in the reaction mixture indicates the presence of the non-quenchable fluorescent cleavage product. With a single quenchable fluorescent cleavage product, a higher fluorescent reading at a temperature greater than the $T_m$ for duplex formation (e.g., where duplexes do not exist) compared to a fluorescence reading at a temperature below the $T_m$ for duplex formation (e.g., where duplexes are formed and stable) indicates the presence of the quenchable fluorescent cleavage product.

Reaction mixtures including more than one different fluorescent cleavage product, where each is subject to quenching by masking oligonucleotide hybridization can conveniently be assessed by processing melting/annealing curve results using derivative analysis to identify $T_m$s of duplexes that may be present in the mixtures. For example, the melting/annealing curve can be processed to calculate first derivatives, and then establish a first derivative plot of change in fluorescence as a function of temperature. Peaks or maxima on the first derivative plot correspond to $T_m$s of duplexes between a masking oligonucleotide and a complementary fluorescent cleavage product. When each of the duplexes is characterized by a different $T_m$, it becomes possible to detect the duplexes independent of each other. Higher order derivatives also are contemplated for identifying duplexes, and determining which of a plurality of FRET cassettes cleaved to generate a fluorescent signal. As described elsewhere herein, it is desirable to have $T_m$s for different duplexes spaced apart by a minimum temperature difference to facilitate distinction of one duplex from the other(s).

Software causing a computer to process results and determine which FRET cassette among a mixture of FRET cassettes produced a cleavage product is embraced by the above description.

EXAMPLES

Illustrated herein are techniques for multiplex detection using at least one 5' flap FRET cassette (i.e., a FRET cassette having a 5' flap portion), where the 5' flap portion thereof harbors a fluorescent label. Signals emitted from the fluorescent label following cleavage of the 5' flap FRET cassette by a FEN-1 endonuclease in an invasive cleavage assay are selectively quenchable on the basis of temperature. In some embodiments, the invasive cleavage assay includes both primary and secondary invasive cleavage reactions. In some other embodiments, the invasive cleavage assay includes secondary invasive cleavage reactions without a primary invasive cleavage reaction. It is to be understood that FEN-1 mediated cleavage physically separates fluorophore and quencher moieties of the 5' flap FRET cassette onto different oligonucleotide molecules, thereby relieving the fluorescent quenching that is characteristic of the intact 5' flap FRET cassette. Quenching of fluorescence emanating from the cleaved 5' flap is mediated by temperature-dependent hybridization of the cleaved 5' flap to a complementary masking oligonucleotide that harbors a quencher moiety. By this approach, the quenchable flap is not part of any probe that hybridizes the target nucleic acid that is to be detected. Instead, the quenchable flap can be the product of a linear amplification reaction that takes place without polymerization under isothermal conditions.

In accordance with the disclosure, the 5' flap FRET cassettes reporting different target molecules can be detected using single-channel fluorescence detection. Fluorescent labels for the different FRET cassettes can be identical fluorescent labels. In some embodiments, the same fluorescent labels are used on FRET cassettes having different 5' flaps. Different fluorescent labels can be used instead of the identical labels, provided that the different labels can be detected in the same fluorescence channel of an optical detector (e.g., a fluorometer). In all instances, cleavage of FRET cassettes to result in fluorescent signals was mediated by a FEN-1 enzyme (i.e., a non-polymerizing flap endonuclease). The cleaved 5' flaps from primary probes served catalytic functions in the cleavage of FRET cassettes, meaning the 5' flaps transiently hybridized to FRET cassettes, promoted cleavage to liberate fluorescent signal, then de-hybridized to allow interaction of the cleaved flap with a new FRET cassette. The 5' flaps cleaved from primary probes that hybridize to the nucleic acid target to be detected preferably do not harbor fluorophore moieties.

Example 1 illustrates how two different nucleic acid sequences (Analyte A and Analyte B) were amplified and detected in the same reaction mixture using either single-channel or dual-channel fluorescence detection. Amplification was by the polymerase chain reaction (PCR). Products of the PCR reaction were detected using invasive cleavage reactions employing fluorescently labeled FRET cassettes. Analyte A was detected using a FRET cassette with a first label (hexachlorofluorescein or "HEX™ dye") that was detectable in the HEX™ dye channel of a fluorometer component of a real-time PCR instrument. Analyte B was detected using either of two different FRET cassettes in the same reaction mixture, where each FRET cassette harbored a different label. A first 5' flap FRET cassette that was used for detecting Analyte B harbored a second label that also was detectable in the HEX™ dye channel of the PCR instrument. The signal emitted by the label joined to the 5' flap cleaved from this FRET cassette indicated the presence of Analyte B, and was subject to quenching after hybridizing the cleaved 5' flap of the FRET cassette to a complementary masking oligo. A second FRET cassette, for detecting Analyte B, harbored a label that was detectable in the ROX™ dye channel of the PCR instrument, where the fluorescent signal emitted following cleavage was not subject to quenching. Notably, signal detected in the ROX™ dye channel of the real-time amplification and detection instrument was not substantially detected in the HEX™ dye channel of the instrument, and vice versa. Stated differently, the fluorescent HEX™ dye signal was not substantially detectable in the ROX™ dye channel, and the fluorescent ROX™ dye signal was not substantially detectable in the HEX™ dye channel. Results established that each of the two analyte nucleic acids could be amplified, and that synthesis of the different amplification products could be monitored using fluorophores detected in the same or different optical channels of a PCR instrument.

Example 1

Single- or Dual-Channel Fluorescence Detection of Two Analyte Nucleic Acids in a Single Reaction Reaction mixtures were prepared as replicates, where each reaction mixture included a lyophilized composition that had been taken up in an aqueous reconstitution buffer. The lyophilized composition included dNTPs, a thermostable DNA polymerase (e.g., Taq DNA polymerase from Promega Corporation; Madison, WI), a FEN-1 flap endonuclease enzyme (e.g., CLEAVASE® 2.0 enzyme from Hologic Inc.; Marlborough, MA), oligonucleotides, and trehalose. Oligonucleotides in the lyophilized composition included, for each of the two analyte nucleic acids to be detected: a pair of primers, a primary probe having a 5' flap that was non-complementary to the analyte sequence to be amplified and/or detected, and a FRET cassette that could be cleaved by a FEN-1 enzyme following hybridization of the 5' flap cleaved from the primary probe. In this example oligonucleotides that promoted cleavage of 5' flaps from the primary probes also served as primers in nucleic acid amplification reactions. Two different primary cleaved flaps (one from each of the primary probes complementary to Analyte A and Analyte B) reversibly hybridized to three different FRET cassettes in an isothermal cycling hybridization reaction. FRET cassette 1 (used for detecting Analyte A) was a flapless FRET cassette labeled with a HEX™ fluorophore and a BLACKBERRY® quencher moiety (Berry & Associates; Dexter, MI). Following cleavage of FRET cassette 1, emission signal from the HEX™ fluorophore was detectable in the HEX™ dye channel of the instrument used to amplify nucleic acids and monitor progress of amplification reactions. FRET cassette 1 did not harbor a 5' flap sequence. FRET cassette 2 was also a flapless FRET cassette that did not harbor a 5' flap, but was labeled with a CAL FLUOR® Red 610 fluorophore (Biosearch Technologies, Inc.; Novato, CA) and a BHQ®-2 quencher moiety (Biosearch Technologies, Inc.), and was used to detect Analyte B. Following the cleavage reaction, emission signal from the CAL FLUOR® Red 610 fluorophore was detectable in the ROX™ dye channel, but not the HEX™ dye channel, of the instrument used to amplify nucleic acids and monitor progress of amplification reactions. FRET cassette 3, also used to detect Analyte B, was a 5' flap FRET cassette labeled on the 5' flap with a CAL FLUOR® Orange 560 fluorophore which was quenched with BHQ® quenching moiety (Biosearch Technologies, Inc.) attached to the hairpin portion. Following the cleavage reaction, emission signal from the CAL FLUOR® Orange 560 fluorophore was detectable in the HEX™ dye channel of the instrument used to amplify nucleic acids and monitor progress of amplification reactions. A masking oligonucleotide complementary to the 5' flap of FRET cassette 3, and comprising a BHQ® quenching moiety (Biosearch Technologies, Inc.), was included in the reaction mixtures at a three-fold molar excess over FRET cassette 3.

The target analytes, FRET cassette configurations, and detection channels used in the procedure are summarized in Table 1.

TABLE 1

| Multiplex Detection System | | | |
|---|---|---|---|
| | HEX™ dye Channel | ROX™ dye Channel | Masking Oligo |
| FRET Cassette 1 (Analyte A) | X | | |
| FRET Cassette 2 (Analyte B) | | X | |
| FRET Cassette 3 (Analyte B) | X | | X |

Amplification reactions employing the detection system presented in Table 1 included either the Analyte A target alone, the Analyte B target alone, or the combination of the Analyte A and Analyte B targets. A "no target" negative control reaction included all reagents but did not include added template. Each reaction included all three FRET cassettes and the masking oligonucleotide. Thermal cycling and fluorescence monitoring were carried out using an ABI 7500 Real-Time PCR System instrument (ThermoFisher Scientific; Grand Island, NY). Reaction conditions included 10 cycles of: 95° C. for 120 seconds, 69° C. for 5 seconds, 67° C. for 5 seconds, 65° C. for 6 seconds, and 72 C for 5 seconds. This was followed by 40 cycles of: 95° C. for 10 seconds, 69° C. for 5 seconds, 67° C. for 5 seconds, 65° C. for 25 seconds. Fluorescent emission data were collected for the ROX™ dye channel and the HEX™ dye channel of the real-time PCR instrument at a temperature where the masking oligo remained unhybridized to released 5' flaps from FRET cassette 3. Fluorescent signals were measured in the HEX™ dye and ROX™ dye channels as a function of cycle number for a reaction that included both of Analyte B and Analyte A. The signal in the ROX™ dye channel (data not shown) resulted in a sigmoid curve reflecting the cycle-dependent increase in signal indicating that Analyte B amplified in the PCR reaction. The HEX™ dye signal reflected combined signal from amplification of Analyte B and Analyte A, but did not distinguish one from the other (data not shown). HEX™ dye and ROX™ dye fluorescent signals were independently detectable in a multiplex reaction that amplified Analyte B and Analyte A.

Figure 5:
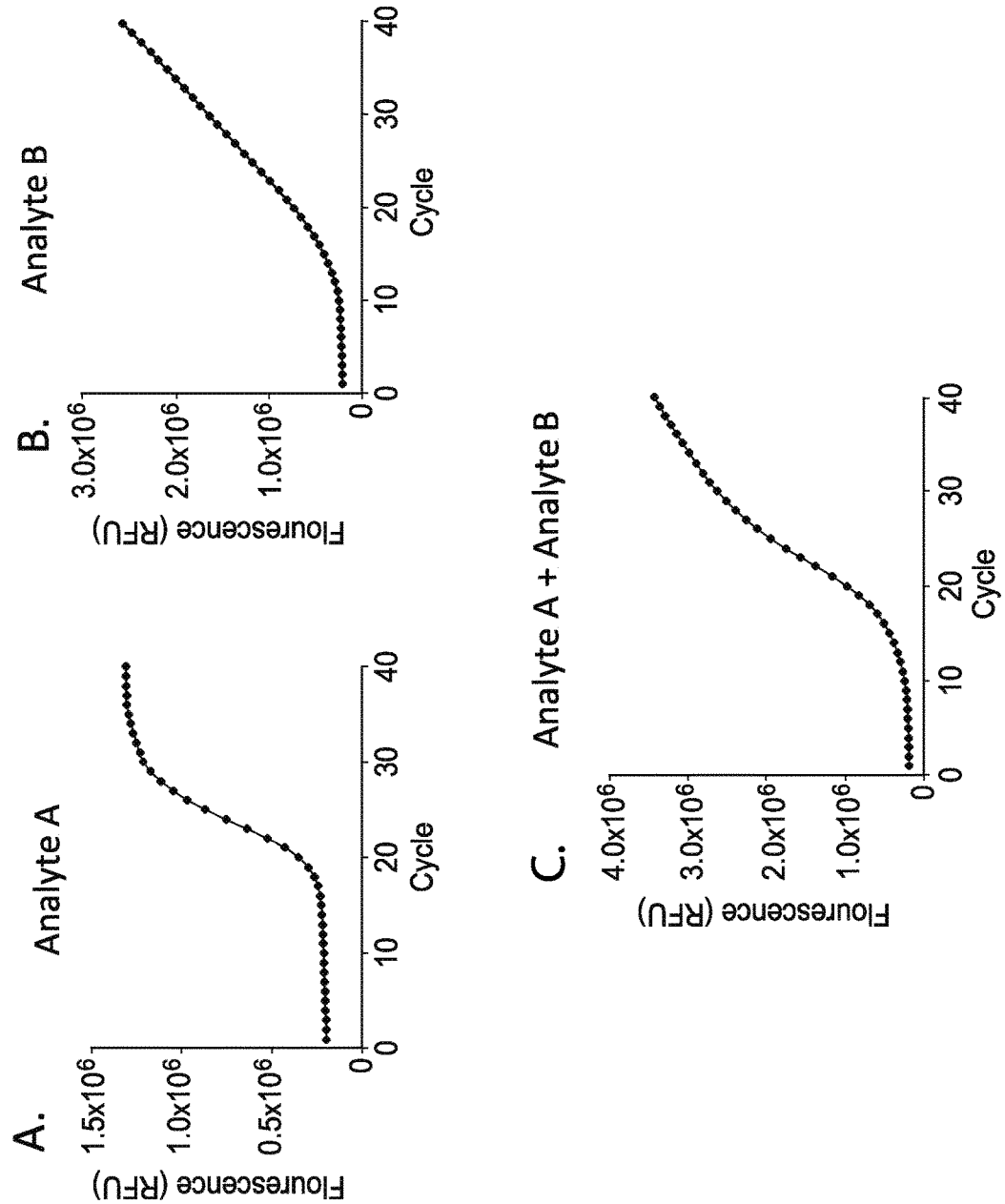
FIG. 5 provides a collection of graphs showing fluorescence measured in the HEX™ dye channel as a function of cycle number. Reactions included either target Analyte A (FIG. 5A), target Analyte B (FIG. 5B), or target Analytes A and B together (FIG. 5C), as described in Example 1.

FIGS. 5A-5C display signals measured in the HEX™ dye channel as a function of cycle number for reactions that included the analytes individually or in combination, as indicated. The graph in FIG. 5A confirmed that amplified Analyte A could be detected in the absence of added Analyte B template, and showed a characteristic sigmoid curve for signal accumulation for this analyte. FIG. 5B displays the signal measured in the HEX™ dye channel that indicated amplification of the Analyte B template in the absence of Analyte A template. The monotonic signal accumulation curve in this instance lacked the sigmoid feature of the curve shown in FIG. 5A. FIG. 5C shows the signal detected in an amplification reaction that included both Analyte A and Analyte B templates in a single reaction. Here the signal measured in the HEX™ dye channel increased in a fashion that produced an extended sigmoid curve, representing the combined signals produced by the Analyte A and Analyte B FRET cassettes measured in a single channel of a fluorometer. In this instance, signals produced by non-identical fluorophores were detected in a single (i.e., the same) channel of the fluorometer. As discussed elsewhere herein, melting/annealing curve analysis, and analysis of curve shape (e.g., first derivative analysis) can be used to deduce identities of analytes giving rise to each different result.

Example 2 illustrates a procedure for resolving the identities of different analyte nucleic acids in the multiplex amplification reaction mixture using a masking oligonucleotide to quench signal from the 5' flap FRET cassette used for detection of Analyte B. Only fluorescence emitted from the label of the cleaved 5' flap complementary to the masking oligo was subject to quenching.

Example 2

End-Point Melting/Annealing Curve Analysis Distinguishes Amplified Targets

Post-PCR reaction mixtures from Example 1 were used for melting/annealing curve analysis on the same real-time PCR instrument that was used for nucleic acid amplification. This involved monitoring the magnitude of the fluorescent signal in the HEX™ dye channel of the real-time PCR instrument as the temperature varied from 90° C. to 21.4° C.

Figure 6:
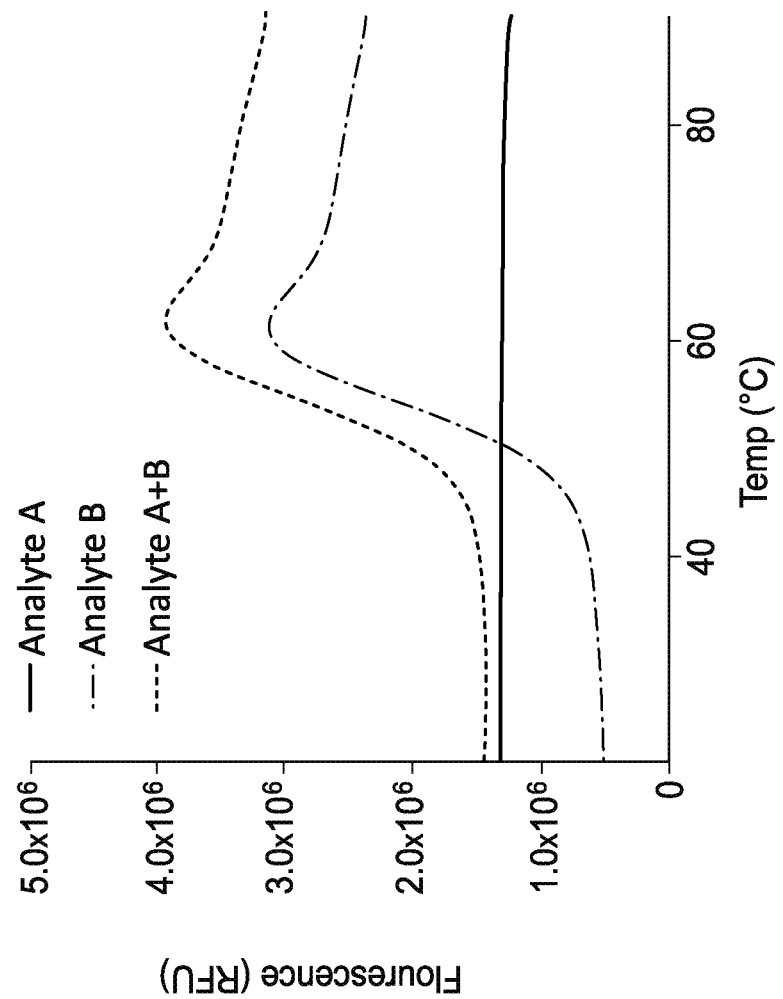
FIG. 6 provides a graph showing melt curve analysis using fluorescence detected in the HEX™ dye channel for reactions containing target Analyte A, target Analyte B, and target Analytes A and B together, as described in Example 2.

Results for the post-amplification melting/annealing curve analysis are presented in FIG. 6. These data confirmed that the cleavage product of the FRET cassette specific for detection of Analyte A, having HEX™ dye-channel signal produced from a flapless FRET cassette that was not quenchable with a masking oligonucleotide, remained uniformly fluorescent as a function of temperature (i.e., across the illustrated temperature range). In contrast, the HEX™ dye-channel signal produced following cleavage of the 5' flap FRET cassette 3 that was specific for detection of Analyte B, in the presence of the masking oligonucleotide that included a quenching moiety, exhibited temperature-dependent fluorescence quenching. More specifically, fluorescence in the reaction mixture spiked with only the Analyte B template was effectively quenched as the temperature approached 20° C., so that fluorescent signal was reduced toward 500,000 RLU. Empirically it was observed that substantially all of the fluorescence was quenched at temperatures just below 40° C. For the reaction that included both Analyte A and Analyte B templates, the signal in the HEX™ dye-channel was essentially the combination of individual temperature profiles. More specifically, the profile of this melting/annealing curve followed the melting/annealing curve for the Analyte B templated reaction, but with the signal increased overall by addition of the unvarying fluorescence arising from the presence of Analyte A in the templated reaction. When the temperature approached 20° C., the signal indicating the presence of Analyte B was quenched, so the fluorescence in the mixed reaction approached the signal level observed in the Analyte A-only reaction. As indicated in the figure, fluorescence was maximal at about 63° C. in reaction mixtures that included the Analyte B template, and was reduced above 63° C. While not wishing to be limited by any particular theory of operation, this reduction in fluorescence above 63° C. may be due to a temperature-dependent buffer effect on the fluorophore, as masking oligo hybridization should be reduced or lost completely at temperatures substantially higher (e.g., 10° C.-20° C. higher) than the $T_m$ of the 5' flap-masking oligonucleotide duplex.

Results obtained using an invasive cleavage system for multiplex detection of nucleic acid analytes, as disclosed herein, can be processed in different ways to determine the presence or absence of analytes in a test sample. For example, fluorescent signals measured at two different temperatures (e.g., 63° C. and 30° C.) in the single channel (e.g., the HEX™ dye-channel of a fluorometer in the present illustration) can be compared to threshold values to establish the presence or absence of each of the two different analytes. Thresholds may be preestablished (i.e., before an assay is conducted), or established at the time an assay is performed (e.g., using one or more calibration standards having one or more analytes to be detected). This analytical method can be illustrated using exemplary thresholds at $2.2 \times 10^6$ RFU, and at $1 \times 10^6$ RFU, and the results from FIG. 6. Under these parameters, a fluorescence reading greater than $2.2 \times 10^6$ RFU at 63° C. indicated detection of Analyte B, while a reading below this threshold indicated the absence of Analyte B. A fluorescence reading between $1.0 \times 10^6$ RFU and $2.2 \times 10^6$ RFU at 63° C. indicated the presence of Analyte A and the absence of Analyte B. Likewise, and alternatively, a fluorescence reading greater than $1 \times 10^6$ RFU at 30° C. indicated the presence of Analyte A. Such a reading would not inform regarding the presence of Analyte B, because fluorescence from the cleaved 5' flap indicating the presence of that analyte was substantially completely quenched at that temperature. A fluorescence reading less than $1 \times 10^6$ RFU at 30° C. would indicate the absence of Analyte A.

A derivative-based data analysis approach can be used either in place of, or in combination with the above-described threshold-based analysis. For example, the data plot associated with the presence of Analyte A (see FIG. 6 as an illustration) has a constant slope (e.g., zero slope) and a fluorescence magnitude at least two-fold greater than background fluorescence of about $5 \times 10^5$ RFU. This fluorescence magnitude (e.g., measured at a temperature where fluorescence quenching in the reaction mixture is maximal could be used to indicate the presence of Analyte A. The data plot associated with the presence of Analyte B exhibited a first derivative maximum in the range of from about 50° C.-58° C., with a zero-point crossing (i.e., x-axis crossing indicating zero slope) at about 63° C. Any data set exhibiting these features could be interpreted as indicating the presence of Analyte B. In some embodiments, fluorescence magnitudes at particular temperatures can be used for threshold-based analysis, and the temperature-dependent rate of change in fluorescence can be used in a derivative-based data analysis, and the two analyses can be combined to make a determination about the presence or absence of each of multiple analytes that may be present in an assay reaction.

Taken together, the foregoing results and discussion demonstrated that unique profiles characterized the melting/annealing curves for each of the three different starting target conditions (i.e., Analyte A only, Analyte B only, or the combination of Analyte A together with Analyte B). These data show that end-point melting/annealing curve analysis using a single detection channel easily resolved which target or targets were present in a reaction mixture.

The preceding Examples demonstrated detection of two different amplified nucleic acid target sequences using invasive cleavage reactions using real-time and endpoint-formatted nucleic acid analyses. Fluorescent signals for the different amplified targets were detected in a single optical channel (i.e., the HEX™ dye-channel) of a fluorometer component of an instrument that monitored nucleic acid amplification as the reaction was occurring (e.g., as a function of time or cycle number). The procedure exploited the fact that the hybrid duplex that included a masking oligonucleotide and a cleaved flap that included a fluorescent label was stable at a temperature below the $T_m$ for the duplex, and unstable above the $T_m$ for the duplex. The results established that maximum quenching was observed at about 39° C., and that minimal quenching was observed at about 63° C. Taken together, the results shown in FIG. 5 and FIG.

6 show how a plurality of different nucleic acid analytes may be detected and resolved from each other in a multiplex reaction mixture using only a single optical channel of a fluorometer. While this was accomplished using different fluorophore species that were detected in the same optical channel of the fluorometer, a single species of fluorophore could have been used instead (e.g., as demonstrated below). Moreover, those having an ordinary level of skill in the art will appreciate how different fluorescent labels can be substituted in place of the exemplary labels described above, and will understand how instrument channels other than the HEX™ dye channel can be used for detection of those labels.

Example 3 describes a procedure for detecting the presence or absence of a plurality of analytes using real-time monitoring and only a single optical channel of a fluorometer of a PCR instrument. Here, the cycling procedure included temperature steps at which fluorescence quenching by the masking oligonucleotide permitted determination of the presence or absence of each of two analytes. More specifically, fluorescence readings were determined at 63° C. and at 39° C. during cycles of the PCR procedure. As demonstrated below, the technique distinguished dual signals measured in a single optical channel in a real-time format. This procedure advantageously can be used for quantitation of each of the detected analytes according to standard procedures for processing real-time amplification run curves by determining the cycle number at which a threshold level of amplification is achieved (e.g., a Ct value). The determined Ct value can then be compared to a calibration plot or equation that relates threshold values and amounts or concentrations of the analyte nucleic acid. An alternative real-time procedure can establish whether an analyte nucleic acid is present in a multiplex reaction mixture above or below a specified (e.g., predetermined) amount or concentration level. This can involve establishing whether a particular level of reaction progress (e.g., measured by Ct value) is achieved by a specified cycle number. Notably, where the previous Example used two different fluorophores that were detected in the same optical channel of a fluorometer linked to a PCR instrument, here two different analytes were detected using the same fluorophore species.

Example 3

Real-Time Monitoring of Multiplex Amplification Using a Single Fluorophore Species Reaction mixtures for the real-time amplification protocol were prepared as follows. Serial dilutions of plasmid DNA that included the Analyte A target sequence were prepared from a standard a stock solution. Wild-type bacterial genomic DNA harboring the Analyte B target sequence served as the source of template nucleic acid for amplification of that analyte. A lyophilized pellet as described under Example 1 was reconstituted using an aqueous buffer, and then spiked with each of the 5' flap FRET cassette specific for detection of Analyte B, and the corresponding masking oligonucleotide. Again, cleavage of FRET cassettes in the reaction mixture was catalyzed by primary cleaved flaps from the primary probes.

Four reaction mixtures were prepared in duplicate using multiwell PCR plates (one plate each to demonstrate high and low temperature monitoring). Negative control mixtures did not receive nucleic acid templates for either Analyte A or Analyte B. The second set of mixtures received only the bacterial genomic DNA that included the Analyte B template, and not the Analyte A plasmid. The third set of mixtures received only the Analyte A plasmid, and not the bacterial genomic DNA containing the Analyte B template. The fourth set of mixtures received both the bacterial genomic DNA containing the Analyte B template, and the Analyte A plasmid. All trials included a three-fold excess of masking oligo over corresponding 5' flap FRET cassette used for detection of Analyte B. PCR reactions with monitoring of fluorescent signal generated by invasive cleavage of FRET cassettes were performed on the ABI 7500 real-time PCR instrument using either a first set of cycling conditions with fluorescence monitoring at 63° C. ("high" temperature monitoring), or a second set of cycling conditions with fluorescence monitoring at 39° C. ("low" temperature monitoring). Cycling conditions used for high-temperature (63° C.) fluorescence monitoring were as follows: (1) 95° C. for 120 seconds; (2) 95° C. for 15 seconds; 69° C. for 5 seconds; 67° C. for 5 seconds; 65° C. for 6 seconds; and 72° C. for 25 seconds×10 cycles (initial Taq optimal stage), and (3) 95° C. for 10 seconds; 69° C. for 5 seconds; 67° C. for 5 seconds; 65° C. for 5 seconds; and 63° C. for 25 seconds×40 cycles. Cycling conditions used for low-temperature (39° C.) fluorescence monitoring were as follows: (1) 95° C. for 120 seconds; (2) 95° C. for 15 seconds; 69° C. for 5 seconds; 67° C. for 5 seconds; 65° C. for 6 seconds; and 72° C. for 25 seconds×10 cycles (initial Taq optimal stage); and (3) 95° C. for 10 seconds; 69° C. for 5 seconds; 67° C. for 5 seconds; 65° C. for 5 seconds; and 39° C. for 25 seconds×40 cycles. Fluorescence monitoring at high and low temperatures was performed for a total of 50 cycles.

Results from the procedure are presented in the real-time PCR amplification plots of FIGS. 7A-7D. The results of greatest interest were trials performed using the Analyte B template alone, or the Analyte B template in combination with the Analyte A template. Reactions using the Analyte A template alone were treated as controls, and are not presented in the figures.

FIGS. 7A and 7B show Analyte B-specific fluorescence as a function of cycle number, where fluorescence was determined in the HEX™ dye-channel of a PCR instrument at 63° C. (no fluorescence quenching) or at 39° C. (fluorescence quenched by a masking oligonucleotide). An increase in fluorescence above background was apparent at 63° C. starting at about cycle 12 and continuing through cycle 40, as shown in FIG. 7A. Fluorescence measurements taken at 39° C. remained substantially at background levels throughout the procedure, as shown in FIG. 7B. These data confirmed that quenching of the Analyte B fluorescent signal was substantially complete at the lower temperature due to hybridization of the cleaved flap to the complementary masking oligonucleotide. Fluorescence observed at the lower temperature (39° C.) in the plot of FIG. 7B was due to background fluorescence, and not due to signal indicating the presence of Analyte B.

FIGS. 7C and 7D show real-time run curve results obtained by monitoring fluorescence signals produced in reactions that amplified and detected the combination of Analyte B and Analyte A template nucleic acids. The curve shown in FIG. 7C, where fluorescence readings were measured during a 63° C. temperature step, reflects the composite contributions from fluorescence produced from cleavage of both FRET cassettes. Only cleavage of the FRET cassette indicating the presence of Analyte B gave rise to a fluorescent flap sequence that could be hybridized by the masking oligonucleotide with the effect of quenching the fluorescent signal at 39° C. As shown in FIG. 7C, the fluorescent signal measured at the 63° C. temperature step (i.e., no fluorescence quenching) started to rise above a background level at about cycle 11, and entered a log-linear phase by about cycle 19. The rate of fluorescence increase began to taper lower by about cycle 29, although the magnitude of the signal continued increasing. The curve shown in FIG. 7D reflects fluorescence readings measured during a 39° C. temperature step. Because the signal from cleaved flap indicating the presence of Analyte B was efficiently quenched at this temperature, the fluorescence measured in FIG. 7D was only from the cleavage reaction indicating the presence of Analyte A.

Taken together, the results presented in FIGS. 7A-7D show that a single reaction mixture could be used for detecting a plurality of target nucleic acids using real-time monitoring of only a single fluorescence detection channel (e.g., monitoring emission from a single fluorophore species), and that each target could be distinguished by monitoring fluorescent emissions at a different temperature. As the disclosed technique is practiced, one temperature corresponded to a condition of fluorescence quenching (i.e., substantially complete or maximal quenching of fluorescence due to a cleaved flap). Detection of Analyte B illustrated this condition. A different temperature in the procedure did not quench fluorescence arising from the cleaved flap.

Although the reactions used to produce results shown in FIGS. 7A-7D were run sequentially on the same instrument (i.e., with fluorescence measurements being made during either a 63° C. step or a 39° C. step), it is preferred that a single reaction mixture is monitored for fluorescence at both temperature steps to simplify detection of a plurality of analytes in the system. Again, this is made possible because detection of the Analyte B signal was effectively removed from double-positive samples (i.e., samples having Analyte B and Analyte A) by fluorescence quenching, thereby leaving only the signal indicating the presence of Analyte A.

As indicated above, results from the real-time monitoring of multiplex reaction mixtures can be used to quantify analyte nucleic acids, or to determine whether an analyte nucleic acid is present in an amount greater than or less than a threshold amount or concentration (e.g., even zero concentration). In some embodiments, quantitation of an analyte nucleic acid may involve comparing a determined Ct value with a calibration plot or equation that relates Ct values and analyte concentrations. In other embodiments, determining whether an analyte nucleic acid is present in an amount greater than or less than a threshold amount or concentration can involve determining whether time-dependent fluorescence values reach a level of reaction progress by a specified time or cycle number. Using data from FIGS. 7A-7D as examples, qualitative determination about the presence or absence of an analyte can involve determining whether a fluorescence reading of at least 500,000 RFU (relative fluorescence units) is achieved by 30 PCR cycles. Fluorescent signal in FIGS. 7B and 7D due to detection of Analyte B have effectively been removed by fluorescence quenching. The increased signal observed in the plot of FIG. 7A compared to the plot of FIG. 7B indicates the contribution of fluorescence due to detection of Analyte B, and so confirms the presence of that target in the reaction mixture. Thus, comparing results from FIGS. 7A and 7B would indicate the reaction mixture contained only Analyte B and not Analyte A. The increased signal observed in the plot of FIG. 7C compared to the plot of FIG. 7D indicates the contribution of fluorescence due to detection of Analyte B in that reaction mixture. Again, remaining fluorescence plotted in FIG. 7D is due to signal arising from detection of Analyte A. Thus, comparing results from FIGS. 7C and 7D would indicate the reaction mixture contained both Analyte A and Analyte B. A similar process can be used to assess the presence or absence of three different analytes.

Example 4 describes a procedure that detected three different analyte nucleic acid sequences in a single reaction mixture using invasive cleavage reactions, where three FRET cassettes were labeled with the same fluorophore (i.e., HEX™ dye). Of course, other fluorophores that can be detected in the same or a different single optical channel of a fluorometer in optical communication with an instrument that amplifies nucleic acids can be used as a substitute for the HEX™ fluorophore.

Example 4

Multiplex Detection of Three Analyte Nucleic Acids Using a Single Type of Fluorophore Invasive cleavage detection of three analyte nucleic acids amplified by PCR was carried out using three different sets of oligonucleotides in the same reaction mixture. Each set of detection oligonucleotides was used to detect a different one of the three analytes (Analyte A, Analyte B, and Analyte C). Each assay reaction employed: (1) a unique primary probe having a target-specific binding sequence and unique 5' flap that was not complementary to the target amplification product that was to be detected; (2) a unique oligonucleotide (referred to as an "invasive primer") that served as an invasive oligonucleotide to cleave the 5' flap from the primary probe when the primary probe was hybridized to its cognate target nucleic acid, and further served as a primer in the amplification reaction; and (3) a unique FRET cassette. Each of the three different FRET cassettes was labeled with a HEX™ fluorophore and a quencher moiety. The FRET cassette used for indicating the presence of Analyte A did not include a 5' flap that was hybridized by any masking oligo in the reaction mixture. More specifically, Analyte A was detected using the invasive primer, primary probe, and flapless FRET cassette of Example 1. FRET cassettes for detecting Analyte B and Analyte C included 5' flap sequences. FRET cassettes, together with associated cleaved flaps from primary probes and masking oligos used in the procedure are illustrated in FIG. 3. The FRET cassette systems for detecting Analytes A, C, and B appear in the upper, middle, and lower portions of the figure, respectively.

The multiplex reaction mixture included two different masking oligonucleotides, one complementary to the 5' flap of the FRET cassette used to detect Analyte B, and one complementary to the 5' flap of the FRET cassette used to detect Analyte C. Each masking oligonucleotide included a quenching moiety at its 5' end. The FRET 5' flap-masking oligonucleotide duplex for Analyte B had a GC content of about 60% and the FRET 5' flap-masking oligonucleotide duplex for Analyte C had a GC content of about 40%. The two duplexes were characterized by different $T_m$s. The cleavage product of the 5' flap FRET cassette used to detect Analyte B and the complementary masking oligonucleotide formed a duplex of greater stability for "high temp" detection, and the cleavage product of the 5' flap FRET cassette used to detect Analyte C and the complementary masking oligonucleotide formed a duplex of lower stability, for "low temp" detection.

Individual reaction mixtures included all assay oligonucleotides (including all three FRET cassettes), together with all reagents needed to carry out PCR amplification of the three analyte nucleic acids, cleavage of primary probes specific for the different analyte nucleic acids, and cleavage of the corresponding FRET cassettes. Reactions included either Analyte A only, Analyte B only, Analyte C only, or the combination of Analytes A and B and C. Thermal cycling conditions were as follows: (1) 95° C. for 120 seconds×1 cycle; (2) 95° C. for 15 seconds, 69° C. for 5 seconds, 67° C. for 5 seconds, 65° C. for 6 seconds, and 72° C. for 25 seconds×10 cycles (initial Taq optimal stage); and (3) 95° C. for 10 seconds, 69° C. for 5 seconds, 67° C. for 5 seconds, and 65° C. for 25 seconds×40 cycles. Post-amplification melting/annealing curve analysis over the range of from 90° C. to 20.7° C. was carried out on an ABI 7500 real-time PCR instrument.

Figure 8:
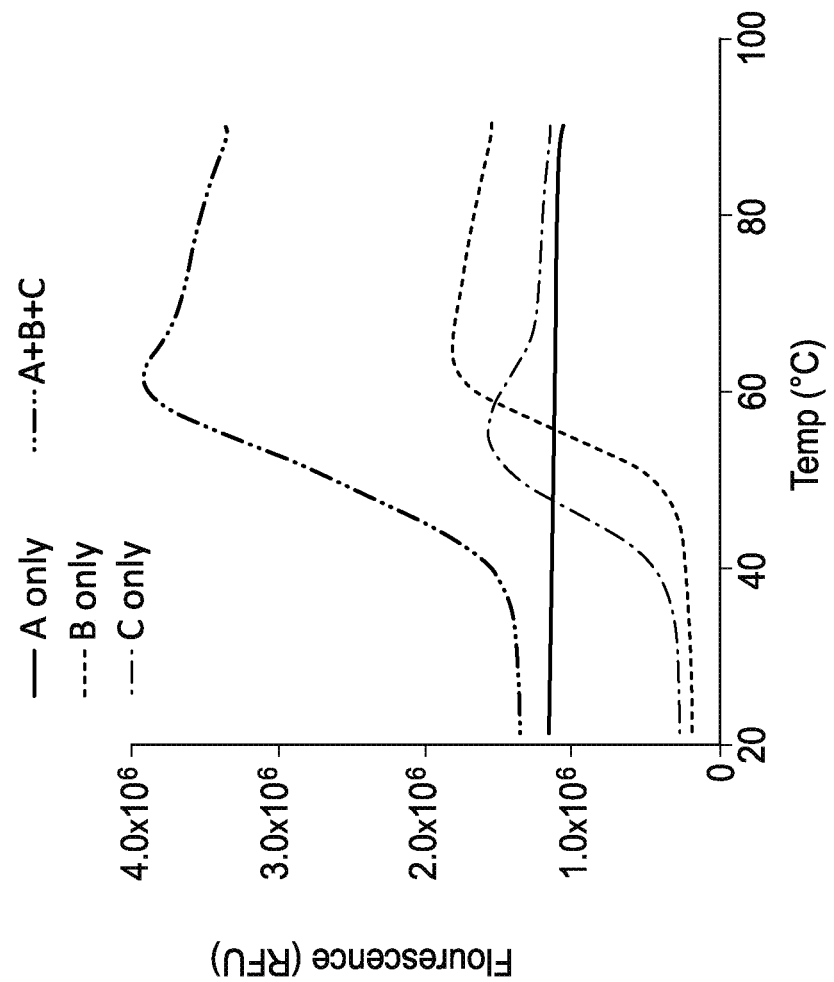
FIG. 8 provides a graph showing melt curve analysis detected in the HEX™ dye channel for reactions containing target Analyte A, target Analyte B, target Analyte C, and the combination of all three target Analytes, as described in Example 4.

FIG. 8 shows the post-amplification melting/annealing curve results for reactions carried out using each of the three analyte polynucleotides, either individually or in combination with each other. The results confirmed that each of the four reactions yielded a unique melting/annealing curve profile, thereby demonstrating success of single-channel multiplexing of three analytes using a single type of fluorophore.

Figure 9:
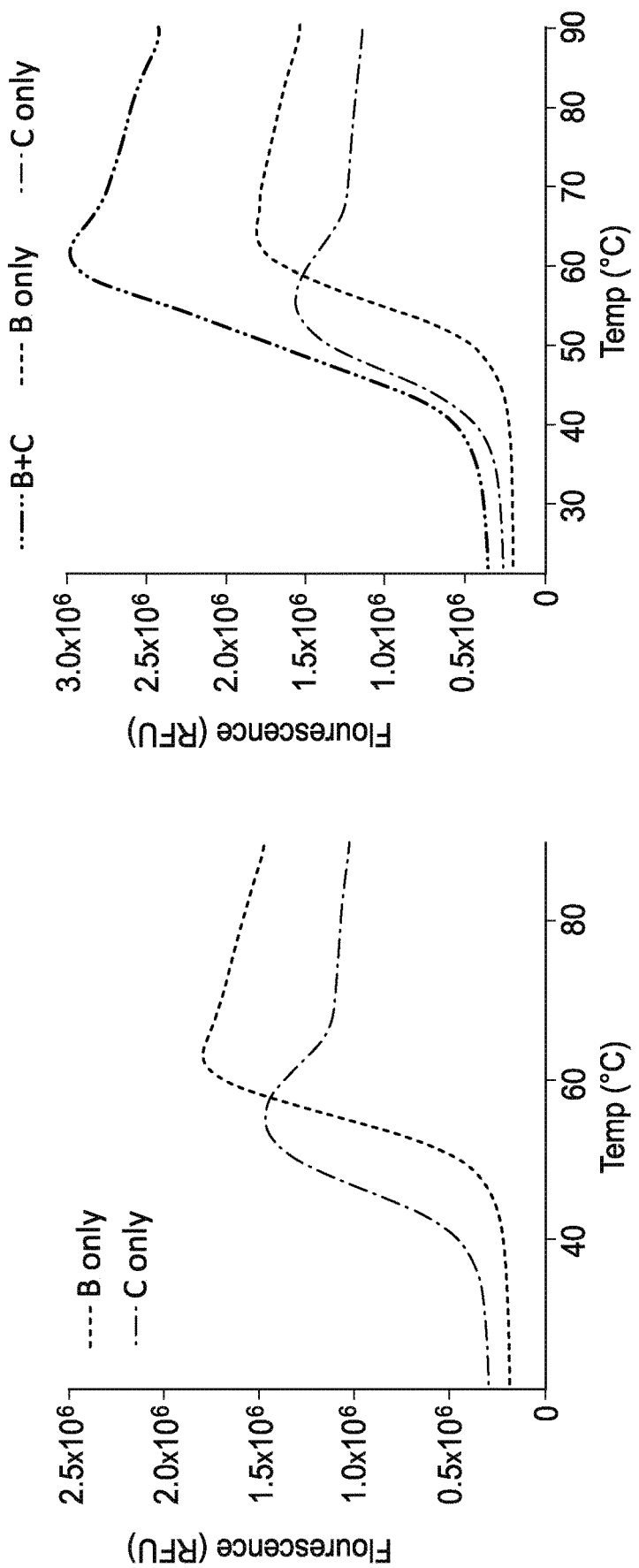
FIG. 9 provides graphs showing unique melting/annealing curve profiles observed for additional analyte combinations, as described in Example 4. The left panel of the figure shows the melting/annealing curve results for reactions that amplified either Analyte B or Analyte C. The right panel of the figure shows the melting/annealing curve analysis results for reactions that amplified Analyte B alone, Analyte C alone, or the combination of Analyte B and Analyte C.

Results shown in the two panels of FIG. 9 illustrate unique melting/annealing curve profiles observed for additional analyte combinations. The left panel of FIG. 9 shows the melting/annealing curve results for reactions that amplified Analyte B and Analyte C individually. The results illustrate how cleaved 5' flaps from each of the FRET cassettes, where the cleaved 5' flaps hybridized to different masking oligos, could be distinguished from each other using only a single fluorescence monitoring channel of the real-time PCR instrument. The right panel of FIG. 9 shows the melting/annealing curve analysis results for reactions that amplified either Analyte B alone, Analyte C alone, or the combination of Analyte B and Analyte C. Again, the results illustrate how cleaved 5' flaps from each of the FRET cassettes, where the cleaved 5' flaps hybridized to different masking oligos, could be distinguished from each other using only a single fluorescence monitoring channel of the real-time PCR instrument.

Figure 10:
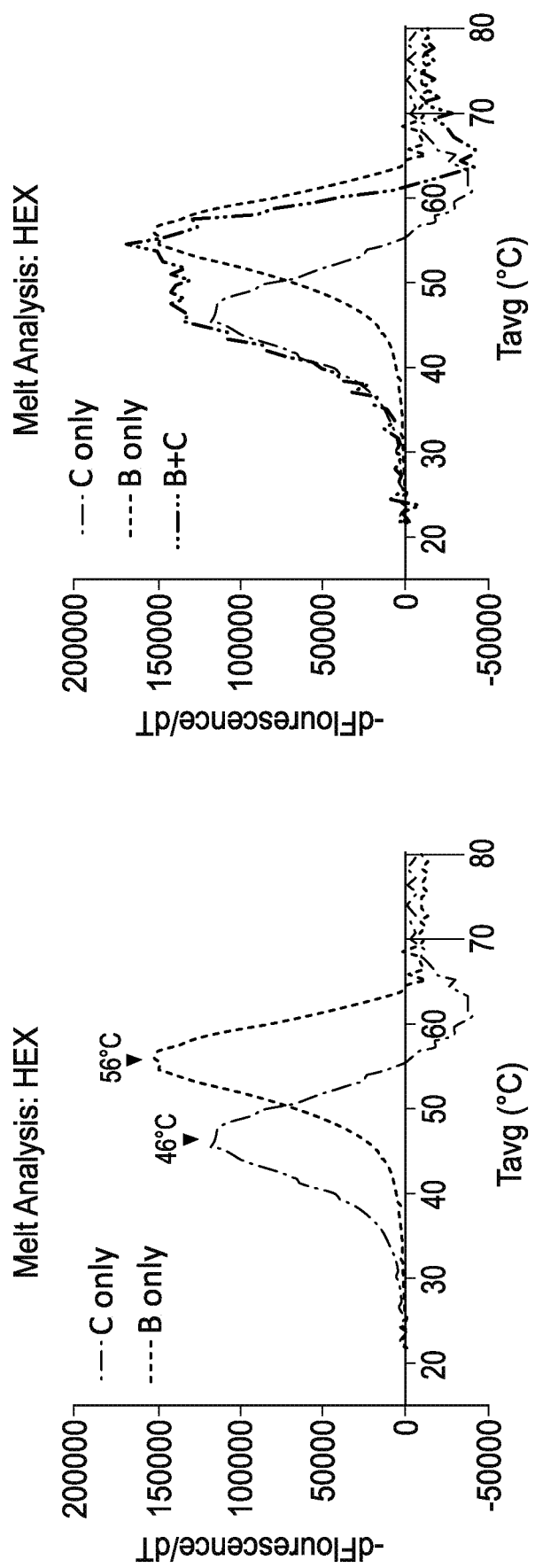
FIG. 10 provides first derivative plots of the measured fluorescence data shown in the two panels of FIG. 9.

FIG. 10 presents first derivative plots of the measured fluorescence data shown in the two panels of FIG. 9. The left panel of FIG. 10 shows a first derivative plot of the melting/annealing curves presented in the left panel of FIG. 9. Maxima of first derivative plots of fluorescence as a function of temperature indicate the melting temperatures ($T_m$s) at which 50% hybridization occurs. In this instance the $T_m$s for the two quenchable targets were separated from each other by about 10° C. (i.e., about 46° C. for detection of Analyte C and about 56° C. for detection of Analyte B). This distinction between the two melting/annealing curves made it possible to resolve which of the two analytes was present in the reaction mixture undergoing analysis. A single maximum observed or detected at about 46° C. would indicate the presence of Analyte C while a single maximum at about 56° C. would indicate detection of Analyte B). The right panel of FIG. 10 shows the first derivative of the melting plots appearing in the right panel of FIG. 9. Each of the different curves had a unique feature that made it possible to distinguish reaction mixtures containing Analyte B, Analyte C, or the combination of Analyte B and Analyte C. Since fluorescent signal arising from the presence of Analyte A is not quenchable as a function of temperature (i.e., there is no masking oligo complementary to the FRET cassette cleavage product), there would be no effect on the first derivative (i.e., first derivative of a constant is zero).

In the instance described above, test samples were analyzed for the presence of two different analytes using derivative analysis of melting/annealing curves. First derivative calculations were used here for illustrative purposes. However, second-order or even higher-order derivative analysis is contemplated for this purpose. The procedure involved detecting or monitoring fluorescent signals in the amplification reaction mixture using only a single channel of a fluorometer component of a real-time nucleic acid amplification apparatus. Plots can present first-derivatives of raw data, but alternatively can present first-derivatives of processed data (e.g., smoothed, normalized to a constant maximal reading, etc.). Detecting a peak or a maximum in the first-derivative plot at 46° C. indicated the presence of Analyte C or amplification products thereof. Detecting a peak or a maximum in the first-derivative plot at 56° C. indicated the presence of Analyte B or amplification products thereof. Detecting peaks at both 46° C. and 56° C. (e.g., high-level signals at both of these temperatures) indicated the presence of both of Analyte C and Analyte B, or amplification products of these analytes. In some embodiments, the analysis can involve identifying signals greater than a threshold (e.g., a pre-established threshold, or a threshold based on fractions or percentages of normalized maxima). While the Example illustrated use of first-derivative analysis, second-derivative analysis can be used instead. Here the maxima on a first-derivative plot would correspond to a zero-crossing point on a second-derivative plot. Detecting the presence of Analyte A did not rely on derivative analysis, because the FRET cassette used for detecting this analyte did not include a 5' flap sequence complementary to any masking oligo. Cleavage of this FRET cassette resulted in a fluorescent signal that remained stable across the temperature range used for the melting/annealing curve analysis. The presence of Analyte A in test samples was reflected by the magnitude of fluorescence at a temperature where signals arising from cleavage of other FRET cassettes (e.g., for detecting Analyte B and/or Analyte C) would be quenched (e.g., at about 30° C. in the plot of FIG. 10).

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in biochemistry, molecular biology, or related fields are intended to be within the scope of the following claims.

What is claimed is:

1. A composition comprising a fluorescence resonance energy transfer (FRET) cassette reporter system, the composition comprising:
   (i) a 5' flap FRET cassette oligonucleotide comprising:
      a 5' flap portion comprising a first fluorophore moiety,
      a stem-loop portion comprising a first quencher moiety,
         wherein fluorescence emission from the first fluorophore moiety of the 5' flap FRET cassette is quenched by the first quencher moiety, and
      a 3' portion comprising a cleaved flap-hybridizing sequence,
         wherein hybridization of a cassette-specific invasive oligonucleotide complementary to the cleaved flap-hybridizing sequence of the 5' flap FRET cassette oligonucleotide forms an invasive cleavage structure cleavable by a flap structure-specific endonuclease-1 (FEN-1) endonuclease at a cleavage site between the first fluorophore moiety and the first quencher moiety,
         wherein cleavage of the 5' flap FRET cassette oligonucleotide at the cleavage site produces a cassette cleaved flap comprising the 5' flap portion and the first fluorophore moiety; and
   (ii) a masking oligonucleotide comprising a second quencher moiety,
      wherein at least a portion of the masking oligonucleotide is specifically hybridizable to the 5' flap portion of the FRET cassette oligonucleotide,
      wherein hybridization of the masking oligonucleotide to the cassette cleaved flap forms a duplex having a first melting temperature exhibiting a first melting peak, and
      wherein fluorescence emission from the first fluorophore moiety in the duplex is quenched by the second quencher moiety.

2. The composition of claim 1, wherein the first quencher moiety and the second quencher moiety are the same as each other.

3. The composition of claim 1, further comprising a FEN-1 endonuclease.

4. The composition of claim 3, wherein the FEN-1 endonuclease is a thermostable FEN-1 endonuclease.

5. The composition of claim 4, wherein the thermostable FEN-1 endonuclease is from an archaeal organism.

6. The composition of claim 1, further comprising a first target-specific invasive oligonucleotide and a first target-specific primary probe oligonucleotide,
   wherein each of the first target-specific invasive oligonucleotide and the first target-specific primary probe oligonucleotide comprise sequences configured to hybridize to a target nucleic acid to form an invasive cleavage structure cleavable by a FEN-1 endonuclease to produce a primary cleaved flap, and
   wherein the primary cleaved flap is a cassette-specific invasive oligonucleotide configured to hybridize to the cleaved flap-hybridizing sequence of the 5' flap FRET cassette oligonucleotide to form an invasive cleavage structure cleavable by the FEN-1 endonuclease.

7. The composition of claim 6, further comprising the target nucleic acid.

8. The composition of claim 7, further comprising deoxynucleoside triphosphates (dNTPs), a thermostable DNA polymerase, and primers having 3' ends extendable by the thermostable DNA polymerase using the target nucleic acid as the template in a template-dependent nucleic acid amplification reaction.

9. The composition of claim 1, further comprising:
   (iii) a second FRET cassette oligonucleotide comprising
     a 5' portion comprising a second fluorophore moiety,
     a stem-loop portion comprising a third quencher moiety, and
     a 3' portion comprising a second cleaved flap-hybridizing sequence,
       wherein hybridization of a second cassette-specific invasive oligonucleotide to the second cleaved flap-hybridizing sequence of the second FRET cassette oligonucleotide forms an invasive cleavage structure cleavable by a FEN-1 endonuclease at a cleavage site between the second fluorophore moiety and the third quencher moiety, and
       wherein cleavage of the second FRET cassette oligonucleotide at the cleavage site produces a second cassette cleavage product comprising the second fluorophore moiety.

10. The composition of claim 9, wherein the second FRET cassette oligonucleotide is a second 5' flap FRET cassette comprising a 5' flap portion, wherein the cassette cleavage product is a second cassette cleaved flap comprising the second fluorophore, and wherein the composition further comprises:
    (iv) a second masking oligonucleotide comprising a fourth quencher moiety,
      wherein at least a portion of the second masking oligonucleotide is specifically hybridizable to the 5' flap portion of the second FRET cassette oligonucleotide,
      wherein hybridization of the second masking oligonucleotide to the second cassette cleaved flap forms a second duplex having a second melting temperature that is higher than the first melting temperature, and
      wherein fluorescence emission from the second fluorophore moiety in the second duplex is quenched by the fourth quencher moiety.

11. The composition of claim 10, wherein the third quencher moiety and the fourth quencher moiety are the same as each other.

12. The composition of claim 9, wherein the second cassette cleavage product comprises no more than 5 nucleotides.

13. The composition of claim 9, wherein the second cassette cleavage product comprises no more than 4 nucleotides.

14. The composition of claim 9, wherein the second cassette cleavage product comprises no more than 3 nucleotides.

15. The composition of claim 9, wherein the second cassette cleavage product comprises no more than 2 nucleotides.

16. The composition of claim 9, wherein emission signals from the first fluorophore moiety and the second fluorophore moiety are detectable in the same fluorescence detection channel of a fluorescence-monitoring apparatus.

17. The composition of claim 9, wherein the first fluorophore moiety and the second fluorophore moiety are the same as each other.

18. The composition of claim 9, wherein the first fluorophore moiety and the second fluorophore moiety are not the same as each other.

* * * * *